United States Patent
Zhou et al.

(10) Patent No.: US 9,706,913 B2
(45) Date of Patent: Jul. 18, 2017

(54) OPTIMIZING VISION CORRECTION PROCEDURES

(71) Applicant: CLARITY MEDICAL SYSTEMS, INC., Pleasanton, CA (US)

(72) Inventors: Yan Zhou, Pleasanton, CA (US); William Shea, Pleasanton, CA (US); Barry Linder, Danville, CA (US)

(73) Assignee: CLARITY MEDICAL SYSTEMS, INC., Pleasanton, CA (US)

( * ) Notice: Subject to any disclaimer, the term of this patent is extended or adjusted under 35 U.S.C. 154(b) by 0 days.

(21) Appl. No.: 14/805,144

(22) Filed: Jul. 21, 2015

(65) Prior Publication Data

US 2015/0320310 A1 Nov. 12, 2015

Related U.S. Application Data

(63) Continuation of application No. 14/471,975, filed on Aug. 28, 2014, now Pat. No. 9,119,561, which is a continuation of application No. 13/902,716, filed on May 24, 2013, now Pat. No. 8,827,452, which is a continuation of application No. 13/354,763, filed on Jan. 20, 2012, now Pat. No. 8,454,162, which is a continuation of application No. 12/605,219, filed on Oct. 23, 2009, now Pat. No. 8,100,530, which is a continuation-in-part of application No. 11/761,890, filed on Jun. 12, 2007, now Pat. No. 7,815,310, which is a continuation-in-part of application No. 11/335,980, filed on Jan. 20, 2006, now Pat. No. 7,445,335.

(51) Int. Cl.
*A61B 3/14* (2006.01)
*A61B 3/10* (2006.01)
*A61B 3/00* (2006.01)
*A61B 3/13* (2006.01)
*A61B 5/00* (2006.01)
*G01J 9/00* (2006.01)
*A61B 3/036* (2006.01)
*A61B 3/103* (2006.01)
*G01J 3/06* (2006.01)

(52) U.S. Cl.
CPC .......... *A61B 3/1015* (2013.01); *A61B 3/0025* (2013.01); *A61B 3/0041* (2013.01); *A61B 3/0091* (2013.01); *A61B 3/036* (2013.01); *A61B 3/10* (2013.01); *A61B 3/103* (2013.01); *A61B 3/1035* (2013.01); *A61B 3/13* (2013.01); *A61B 3/14* (2013.01); *A61B 5/7415* (2013.01); *G01J 9/00* (2013.01); *G01J 2003/064* (2013.01)

(58) Field of Classification Search
USPC .................................................. 351/200–246
See application file for complete search history.

(56) References Cited

U.S. PATENT DOCUMENTS 8,002,410 B2 * 8/2011 Shea ................. G01J 9/00
351/205
8,100,530 B2 * 1/2012 Zhou ................. G01J 9/00
351/205

(Continued)

*Primary Examiner* — Mohammed Hasan
(74) *Attorney, Agent, or Firm* — Kilpatrick Townsend & Stockton LLP

(57) ABSTRACT

In one embodiment, a wavefront sensor is combined with a slit lamp eye examination device so that real time aberration values of an eye being examined can be viewed during a slit lamp eye examination session.

23 Claims, 14 Drawing Sheets

(56) References Cited

U.S. PATENT DOCUMENTS

2003/0223037 A1\* 12/2003 Chernyak ............ A61B 3/1015
 351/209
2008/0106633 A1\* 5/2008 Blum ....................... G02C 7/08
 348/345
2012/0078240 A1 3/2012 Spooner \* cited by examiner Cross section of the wavefront with different defocus offset 1112   1113   1114   1115   1116

1132   1133   1134   1135   1136

2D dot pattern representing local tilt of subwavefront sampled around an annular ring 1122   1123   1124   1125   1126

Vertical cross section of the wavefront with different defocus offset 1212  1213  1214  1215  1216

Horizontal cross section of the wavefront with different defocus offset 1222  1223  1224  1225  1226

1242  1243  1244  1245  1246

2D dot pattern representing local tilt of subwavefront sampled around an annular ring 1232  1233  1234  1235  1236

OPTIMIZING VISION CORRECTION PROCEDURES

CROSS-REFERENCE TO RELATED APPLICATIONS

This application is a continuation of U.S. patent application Ser. No. 14/471,975 entitled "Optimizing Vision Correction Procedures", filed on Aug. 28, 2014; which is a continuation of U.S. patent application Ser. No. 13/902,716 entitled "Optimizing Vision Correction Procedures" filed on Jan. 20, 2012, now U.S. Pat. No. 8,827,452 (issued Jun. 4, 2013); which is a continuation of U.S. patent application Ser. No. 13/354,763 entitled "Optimizing Vision Correction Procedures", filed on Jan. 20, 2012, now U.S. Pat. No. 8,454,162 (issued Jun. 4, 2013); which is a continuation of U.S. patent application Ser. No. 12/605,219 entitled "Optimizing Vision Correction Procedures" filed Oct. 23, 2009, now U.S. Pat. No. 8,100,530 (issued Jan. 24, 2012); which is a continuation-in-part of U.S. patent application Ser. No. 11/761,890 entitled "Adaptive Sequential Wavefront Sensor an its Applications", filed Jun. 12, 2007, now U.S. Pat. No. 7,815,310 (issued Oct. 19, 2010); which is a continuation-in-part of application Ser. No. 11/335,980 entitled "Sequential Wavefront Sensor" filed Jan. 20, 2006, now U.S. Pat. No. 7,445,335 (issued Nov. 4, 2008); all of which are incorporated by reference for all purposes.

TECHNICAL FIELD

One or more embodiments of the present invention relate generally to ophthalmic wavefront sensors and adaptive optics systems. In particular, the invention is related to wavefront guided vision correction procedures.

BACKGROUND OF THE INVENTION

A wavefront sensor is a device for measuring the aberrations of an optical wavefront. Wavefront sensors have been used for eye aberration measurement by directing a narrow beam of light to the retina of an eye and sensing the optical wavefront coming out from the eye. For a relaxed emmetropic eye or a relaxed eye with aberrations completely corrected, the optical wavefront coming out from the eye is planar. If, on the other hand, the eye has optical aberrations, the wavefront coming out from the eye in a relaxed state will depart from being planar.

Traditional vision diagnostic, vision corrective and surgical refractive procedures, including auto-refraction, standard eye wavefront measurement, phoropter test, LASIK (Laser Assisted In-Situ Keratomileusis), LTK (Laser Thermokeratoplasty), SBK (Sub-Bowmans Keratomileusis), IntraLASIK (Intra-stromal corneal lenticule extraction), PRK (photorefractive keratectomy), LASEK (Laser Assisted Sub-Epithelium Keratomileusis), IOL (Intraocular lens, including multi-focal, accommodating and toric IOL) implantation, corneal onlay/inlay implantation/positioning, RK (Radial keratotomy), LRI (Limbal Relaxing Incision), CRI (Corneal Relaxing Incision), and AK (Arcuate Keratotomy), are generally conducted without any continuous wavefront measurement result being displayed in real time to the clinical practitioner to show the effect of the correction in real time (see for example U.S. Pat. No. 6,271,914, U.S. Pat. No. 6,271,915, U.S. Pat. No. 6,460,997, U.S. Pat. No. 6,497,483, and U.S. Pat. No. 6,499,843). Although wavefront sensors have been used to measure the refractive errors and higher order aberrations of the eye before, during, and after the dynamic vision correction process, these devices generally only produce a static snapshot display of the wavefront map of the measurement, thereby potentially missing information vital to the practitioner for optimization of the optical outcome.

SUMMARY OF THE INVENTION

One example embodiment is an apparatus for optimizing vision correction procedures comprising: a narrow beam of light directed to a patient's retina; a dynamic defocus offsetting device configured to offset the defocus of a wavefront from an eye; a wavefront sensor configured to measure the local tilt of a number of subwavefronts sampled around an annular ring (the diameter of which can be dynamically changed) over the wavefront with the defocus offset; and a display device configured to display a two dimensional (2D) centroid data points pattern in real time with each data point position representing a corresponding local tilt of the sampled subwavefronts.

Another embodiment is a method for optimizing vision correction procedures comprising: directing a narrow beam of light to a patient's retina; dynamically offsetting the defocus of a wavefront from the patient's eye; measuring with a real time wavefront sensor the local tilt of a number of subwavefronts sampled around an annular ring (the diameter of which can be dynamically changed) over the wavefront with the defocus offset; and displaying a two dimensional (2D) centroid data point pattern in real time with each data point position representing a corresponding local tilt of the sampled subwavefronts.

Extending the general concept of offsetting some wavefront aberration components based on a real time wavefront measurement feedback to allow the remaining aberration components to show up more clearly, one embodiment is an apparatus for optimizing vision correction procedures comprising: a narrow beam of light directed to a patient's retina; a wavefront offsetting element configured to dynamically offset only certain aberration components of a wavefront from the patient's eye; a real time wavefront sensor configured to measure the local tilt of a number of subwavefronts sampled according to a certain sampling pattern over the wavefront with the offset; and a feedback means configured to guide the offsetting.

Another embodiment is a method for optimizing vision correction procedures comprising: directing a narrow beam of light to a patient's retina; dynamically offsetting only certain aberration components of a wavefront from the patient's eye with a wavefront offsetting element; measuring with a real time wavefront sensor the local tilt of a number of subwavefronts sampled according to a certain sampling pattern over the wavefront with the offset; and guiding the offsetting with a feedback means.

One aspect of the present invention is the active offsetting rather than a mere passive compensation of some wavefront aberration component(s) from an eye. The offset can be implemented using a simple focal length variable lens or an equivalent, or a more complicated wavefront manipulator. A key differentiation from prior arts is the active part of the offsetting. The offset can be scanned and the deliberate offsetting can be applied to one or more particular aberration component(s) in a dynamic manner.

Another aspect of the present invention is the involvement of the end user or the control of a built-in algorithm in determining the amount or range of the offset to be applied based on the real time wavefront measurement feedback. One purpose is to highlight the key features of those wavefront aberration components that need to be further corrected during a vision correction procedure. Another purpose is to average out noise and obtain a better measurement of the aberration of the eye.

Still another aspect of the present invention is the unique way to sample the wavefront and display the real time measurement result in a manner that a refractive surgeon can easily understand. In particular, by sampling around an annular ring of the wavefront with a certain defocus offset or a scanning of the defocus offset, a 2D centroid data point pattern can be generated that can be fitted to an ellipse, with a circle and a straight line being the extreme case of an ellipse, and in doing so a direct representation of the sphero-cylindrical refractive errors can be achieved.

Still another aspect of the invention is to dynamically change the annular ring size selected for wavefront sampling so that while an easy to understand 2D centroid data point pattern is presented to the end user, the sampling can also cover most of the wavefront if needed. Built-in algorithms can be used to take into consideration the annular ring size change and to still present an ellipse or a diagram that is a typical representation of spherical and cylindrical refractive errors as is well understood by vision correction practitioners.

Still another aspect of the invention is to sample the wavefront according to a sampling pattern while offsetting some lower order aberrations so that information on some particular higher order wavefront aberrations can be clearly highlighted or vice versa. For example, by dynamically offsetting defocus and compensating astigmatism, higher order aberration (HOA) content, such as coma, which is a very prevalent HOA that surgeons are becoming familiar with and have techniques to address surgically, can be highlighted and displayed in a format easily understandable by clinical practitioners.

One object of the present invention is to guide IOL placement intra-operatively, and then confirm while still in the operating room, the optimal centration, tilt, circumferential angular orientation (in the case of any lens with toricity), and refractive results (i.e. to confirm emmetropia intra-operatively, or any other refractive endpoint goal for the patient). More specifically, the 2D centroid data point pattern can be used to guide the reduction of tilt imparted by an IOL; when a multi-focal IOL is being implanted, the presently disclosed apparatus can be used to control and change the sampled annular ring size to check the focus range of the implanted multi-focal IOL; when an accommodative intra ocular lens (AIOL) is being implanted, the presently disclosed apparatus can be used to measure whether an implanted AIOL can provide the desired accommodation range; when a toric IOL is being implanted, the presently disclosed apparatus can be used to guide the centration and circumferential angular orientation positioning of the toric IOL.

Another object of the present invention is to confirm if the optical power of the IOL selection is correct, especially for patients with post-op corneal refractive procedures, for whom the pre-surgery IOL selection formulas do not deliver consistent results.

Still another object of the present invention is to shape and position corneal onlay and/or inlay ex-vivo or in-vivo.

Still another object of the present invention is to guide and optimize corneal material removal based vision correction surgical procedures using the real time feedback with the offsetting property, such surgical procedures include LASIK, SBK, LTK, IntraLasik, FlEXi Lasik, PRK, LASEK, RK, LRI, CRI, and AK.

Still another object of the present invention is to confirm the aphakic condition throughout the entire corneal visual field through dynamically changing the annular ring size.

Still another aspect of the invention is to combine a real-time wavefront sensor and slit lamp eye examination device so that real time aberration values can be viewed when a patient's eye is examined using a slit lamp eye examination device.

These and other features and advantages of the present invention will become more readily apparent to those skilled in the art upon review of the following detailed description of the embodiments taken in conjunction with the accompanying drawings.

DETAILED DESCRIPTION OF EXAMPLE EMBODIMENTS

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, various embodiments may be practiced without some or all of these specific details. In other instances, well known process operations have not been described in detail in order not to unnecessarily obscure the present invention. Further, each appearance of the phrase an "example embodiment" at various places in the specification does not necessarily refer to the same example embodiment.

Figure 1:
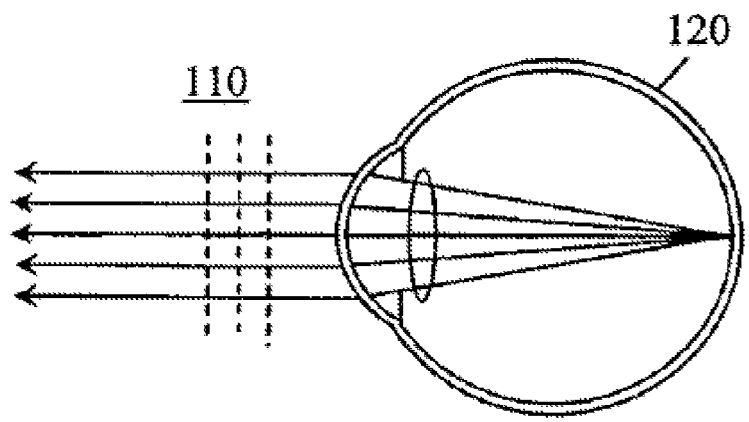
FIG. 1 shows planar wavefront coming out from an emmetropic eye that is in a relaxed state.

An eye without any optical aberration is called an emmetropic eye and the normal aberration-free vision or sight is called emmtropia. In such an eye with perfect vision, the rays of light from a distant object can be brought into sharp focus on the retina while the eye is relaxed. This is what you want with laser or other vision correction procedures. Since for a distant object, the wavefront entering a relaxed emmetropic eye can be considered planar, when the light ray propagation direction is reversed, i.e. when light rays emitted from a point source near the fovea travels backward through the eye optics system and leaves the eye, the wavefront is also planer. FIG. 1 shows the planar wavefront 110 coming out from a relaxed emmetropic eye 120.

Figure 2:
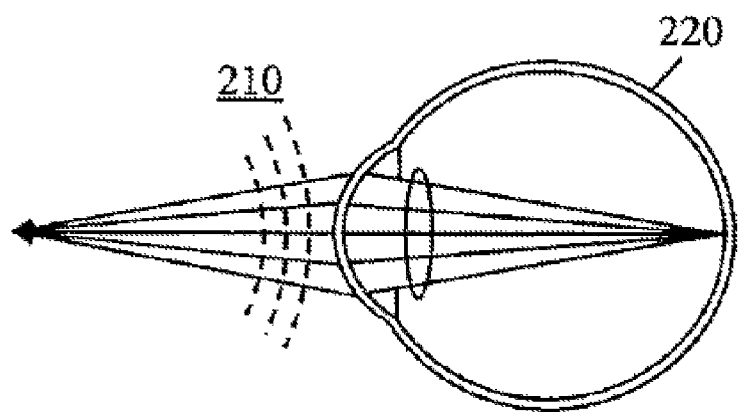
FIG. 2 shows convergent spherical wavefront coming out from a myopic or nearsighted eye.
Figure 3:
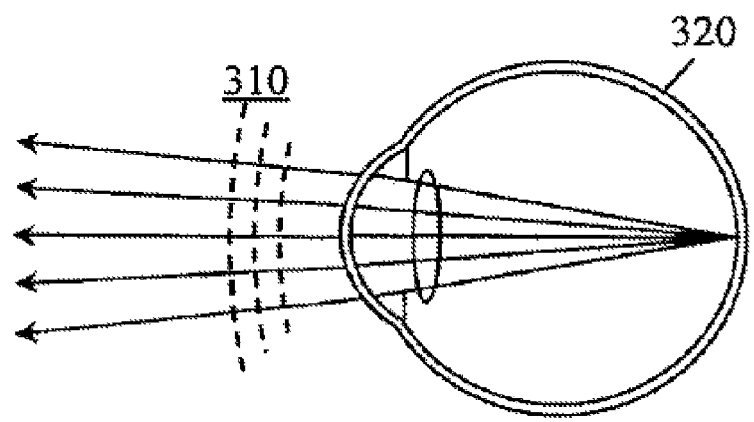
FIG. 3 shows divergent spherical wavefront coming out from a hyperopic or farsighted eye.

Eyes aberrations are traditionally classified as low order and high order. Low-order aberrations include defocus (also called spherical refractive error) and astigmatism (also called cylindrical refractive error). More familiar names for two different types of defocus are nearsightedness (myopia) and farsightedness (hypermetropia or hyperopia). These refractive errors can be measured with an autorefractor, and they make up about 85 percent of all aberrations in an eye. When light rays emitted from a point source near the fovea travel backward through the eye optics system that has defocus and leaves the eye, the wavefront is either spherically convergent or spherically divergent. FIG. 2 shows the convergent spherical wavefront 210 coming out from a myopic or nearsighted eye 220 and FIG. 3 shows the divergent spherical wavefront 310 coming out from an hyperopic or farsighted eye 320.

If there is no astigmatism, the cornea of the eye is shaped like the cross section of a baseball cut in half. The curvature or steepness of the half-dome is the same all the way around. Compare this to a cornea which is similar to a football cut in half lengthwise (in the long direction, through both pointy ends). The curvature of the cornea in the long direction (along the seams) is not as steep as along the short direction. Such a cornea focuses light, not at a single point, but at 2 points. Someone who has uncorrected astigmatism may see images that are fuzzy and doubled. A cornea shaped like a football, cut lengthwise, has astigmatism.

In an eye with astigmatism, the rays of light from a distant object are brought into focus along two perpendicular orientation directions at two different points, for example, one on the retina and the other, behind the retina. This can be the case of an eye with a cornea that has astigmatism, a non-uniform curvature like the football cut lengthwise. The two different curvatures results in two different focal points. There are several different combinations of astigmatism, depending on where the focal points are located. Examples include:

Simple myopic astigmatism: One point in front of retina, the other on the retina;
Compound myopic astigmatism: Both points of focus in front of the retina;
Simple hyperopic astigmatism: One point behind the retina, the other on the retina;
Compound hyperopic astigmatism: Both points of focus behind the retina;
Mixed astigmatism: One point in front of the retina, the other behind the retina;

Often, when astigmatism occurs inside the eye as well as at the cornea, the astigmatism inside the eye is just opposite in amount to the corneal astigmatism. The two forms of astigmatism can thus cancel each other and leave the eye with no significant amount of astigmatism.

An astigmatic eye generally has two different meridians, at 90° to each other, which cause images to focus in different planes for each meridian. The meridians can each be myopic, hyperopic, or emmetropic. The correction for astigmatism is generally a cylindrical or toric lens with different light ray focusing powers at different particular orientation directions.

Astigmatism causes images to be out of focus no matter what the distance. It is possible for an astigmatic eye to minimize the blur by accommodating, or focusing to bring the "circle of least confusion" onto the retina.

In order to correct astigmatism, the location of the axis of a cylindrical lens must be specified when it is placed before or inside the eye. In designating the angle of the axis, the observer faces the patient and the orientation angle zero is at the observer's left. The scale is read below the horizontal line with 90° at the bottom and 180° at the right.

For the case of an astigmatic eye or an eye with cylindrical refractive error, the wavefront coming out from a point light source near the fovea of the eye will no longer be rotationally symmetric relative to the optical axis and instead, the wavefront will have different spherical divergence or convergent along two different but mutually perpendicular azimuthal orientation directions.

Figure 4:
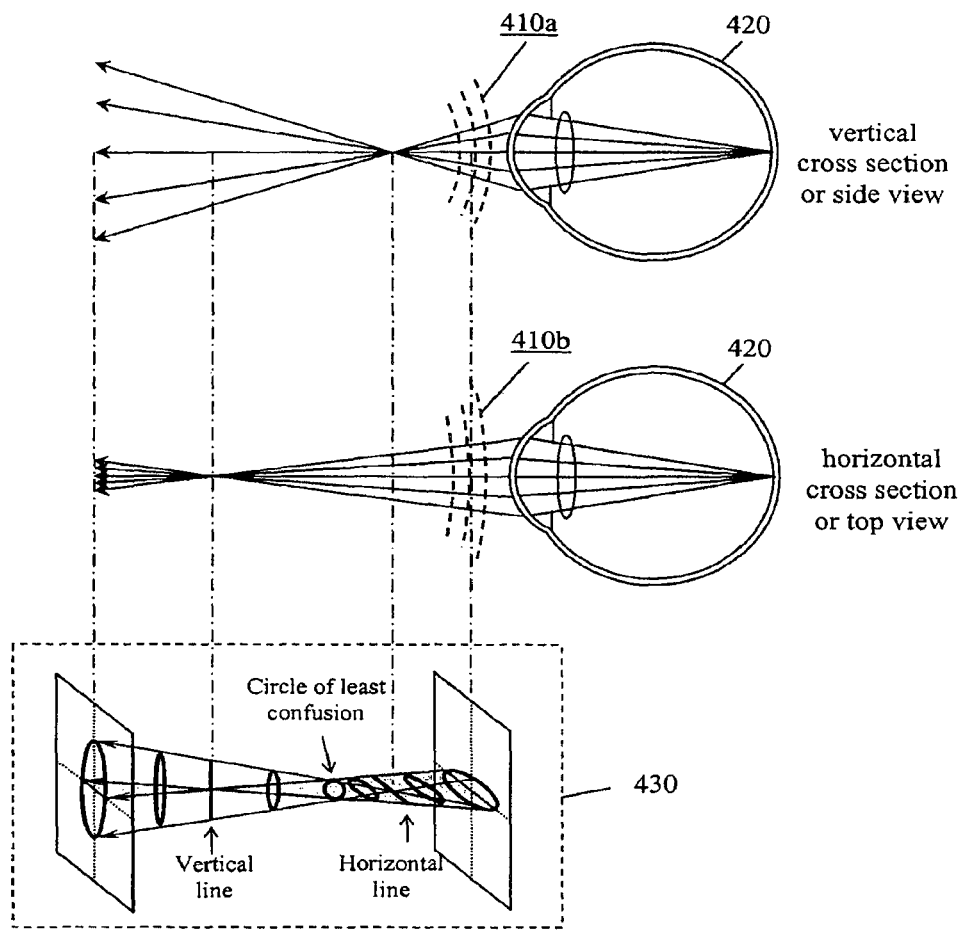
FIG. 4 shows the wavefront coming out from an eye that is nearsighted but also with astigmatism.

FIG. 4 shows the wavefront coming out from an eye 420 that is nearsighted but also with astigmatism (compound myopic astigmatism). Note that the degree of convergence of the wavefront after leaving the eye is different for the vertical (side view) and the horizontal (top view) cross sections. The vertical cross sectional wavefront 410a for the side view case is initially more convergent after the light rays leave the eye than the horizontal cross sectional wavefront 410b is for the top view case. Correspondingly, the beam shape will also no longer be purely conical with rotational symmetry around the optical axis. As shown by the three-dimensional illustration of 430, following the light propagation from the right to the left, the beam cross-sectional shape (perpendicular to the beam propagation direction) will change from a larger horizontal ellipse, to a horizontal line, to a smaller horizontal ellipse with a shorter major axis, to a circle of least confusion, to a smaller vertical ellipse with a shorter major axis, to a vertical line, then to a larger vertical ellipse. It should be noted that these shapes are for the beam cross sections that should not be confused with the two dimensional (2D) wavefront centroid data point pattern to be discussed below, although there is a correspondence or similarity between the two.

As for the wavefront, it is necessary to note that the geometric ray optics representation is not accurate. As a beam gets focused near the best focus position, wave optics should be used to figure out the wavefront changes. In fact, the beam behaves more like a Gaussian beam near the best focus region and the curvature of the wavefront will not remain the same but will change gradually from a convergent wavefront to a slightly more convergent wavefront, then to a less convergent wavefront and finally to a planar one and then to a divergent wavefront. At the horizontal line beam shape position, the side view or vertical cross sectional wavefront is actually planar because this is the point at which the corresponding vertical cross sectional wavefront is changing from a convergent spherical wavefront to a divergent spherical wavefront. Similarly, at the vertical line beam shape position, the top view or horizontal cross sectional wavefront will be planar because this is the position at which the corresponding horizontal cross sectional wavefront is changing from a convergent spherical wavefront to a divergent spherical wavefront. We will give a more detailed discussion on the correspondence between beam shape change and the association wavefront change later.

It should be noted that visual acuity and visual performance are related to wavefront aberrations, but the metrics used to describe vision is not the same as a glasses or contact lens prescription which can be taken to an optical shop to be filled. Vision is usually given in the Snellen format, for example, 20/40. For 20/40 vision, an object that can be seen by a patient 20 feet away, can be seen from 40 feet away by someone who has 20/20 vision. Therefore, someone with 20/400 vision has even worse vision; the larger the denominator or the second number, the poorer the vision. In the extreme, if the vision is even worse, such that a person cannot see the biggest letter "E" on the eye chart, the number of fingers that can be counted is a way of measuring vision. If someone has "counting fingers at 3 feet", it means the eye in question has worse than 20/400 vision, and can only identify the number of fingers held 3 feet away. The gold standard of perfect vision has been 20/20 vision, though there are patients capable of seeing better than "perfect". While most patients use both eyes together, vision is tested in each eye separately, as is the measurement of a person's prescription. The table below shows the relationship between visual acuity (in feet and meters) and refractive error in diopters, which is a unit of measurement of the optical power of a lens, equal to the reciprocal of the focal length measured in meters (that is, 1/meters).

| Visual Acuity in Feet | Visual Acuity in Meters | Refractive Error in Diopters |
|---|---|---|
| 20/20 | 6/6 | 0.00 |
| 20/30 | 6/9 | −0.50 |
| 20/40 | 6/12 | −0.75 |
| 20/50 | 6/15 | −1.00 |
| 20/70 | 6/20 | −1.25 |
| 20/100 | 6/30 | −1.50 |
| 20/150 | 6/45 | −2.00 |
| 20/200 | 6/60 | −2.50 |
| 20/250 | 6/75 | −3.00 |

In terms of prescription for vision correction, if an eye is just nearsighted, there will be a single negative diopter number. The minus sign indicates nearsightedness or myopia. The number that comes after the minus sign tells the amount or "severity" of the nearsightedness. For examples a −1.00 D means one diopter of nearsightedness, a −5.25 D means 5.25 or 5 and ¼ diopters of nearsightedness. This is more nearsighted than −1.00 D, and so thicker negative glasses are needed.

If an eye is just farsighted, there will be a single positive diopter number. The plus sign indicates farsightedness or hyperopia. The number that comes after the plus sign tells the amount or "severity" of the farsightedness. For examples, a +1.00 D means one diopter of farsightedness, a +5.75 D means 5.75 or 5 and ¾ diopters of farsightedness. This is more farsighted than +1.00 D, and so thicker positive glasses are needed.

If an eye has astigmatism, the numbers are harder to follow. There are actually 3 numbers in a prescription for an eye that has astigmatism. The general form is S+C×Axis. Both S and C can be either positive or negative numbers. S refers to what is called the "sphere" or spherical portion of the prescription. The C refers to the amount of astigmatism or cylindrical portion of the prescription. The Axis is a number anywhere between 0 and 180 degrees; this axis number tells where the difference in corneal curvature occurs or how the astigmatism is oriented or aligned. It is not enough to specify how much astigmatism there is, it is necessary to know where the difference in curvature is taking place, by giving coordinates. Accordingly, there are three numbers in a prescription for astigmatism of some kind and severity. The bigger the second number, C, the more astigmatism there is. There are several categories of astigmatism, and by analyzing the 3-numbered prescription, the exact type of astigmatism is specified. For examples, −2.00+1.50×180 means a minus 2 diopter of spherical refractive error with a plus 1.50 diopter of astigmatism at an axis of 180 degrees; +4.00+3.00×89 means a plus 4 diopter of spherical refractive error with a plus 3 diopter of astigmatism at an axis of 89 degrees.

Higher-order aberrations refer to other distortion acquired by a wavefront of light when it passes through an eye with irregularities of its refractive components (tear film, cornea, aqueous humor, crystalline lens and vitreous humor). Abnormal curvature of the cornea and crystalline lens may contribute to higher order aberrations (HOA). Serious higher-order aberrations also can occur from scarring of the cornea from eye surgery, trauma or disease. Cataracts clouding the eye's natural lens also can cause higher-order aberrations. Aberrations also may result when dry eye diminishes eye's tear film, which helps bend or refract light rays to achieve focus. Some names of higher order aberrations are coma, trefoil and spherical aberration. Higher order aberrations can be measured using a wavefront sensor and they make up about 15 percent of the total number of aberrations in an eye.

In spite of the fact that wavefront sensors have been used to make measurement before a vision correction which can provide a prescription for the vision correction procedure, and a snapshot of the wavefront measurement result during or after the vision correction procedure can tell the vision correction practitioner if the correction is progressing or done properly, the static or snapshot nature of the wavefront map cannot instantaneously guide or titrate the vision correction procedure in real time to optimize the vision correction outcome. The lack of real time objective feedback often leads to the need for one or more follow-up procedure(s) to trim or fine-tune the vision correction, which is costly, inherently risky, time consuming and troublesome to both the eye doctor and the patient.

Even though there are disclosures on controlling laser based refractive procedures using wavefront measurement in a closed loop fashion (see for example, U.S. Pat. No.

6,428,533, U.S. Pat. No. 6,887,232, U.S. Pat. No. 7,232,463, U.S. Pat. No. 6,394,999, and U.S. Pat. No. 6,508,812) and also on displaying the wavefront measurement result in real time (see for example, U.S. Pat. No. 6,572,230, U.S. Pat. No. 6,609,794, and U.S. Pat. No. 6,631,991), the control and display are not user-friendly because the closed loop control does not give the clinical practitioner the freedom to optimize the vision correction procedure in real time and the display is not in a format that can be easily understood by the practitioner. Furthermore, previous wavefront sensor based adaptive optics systems that have incorporated wavefront compensator(s) generally operate in an on/off manner to only allow the end user to turn the wavefront compensator(s) on or off to compensate some lower orders of or all of the aberrated eye wavefront (see for example, U.S. Pat. No. 5,777,719, U.S. Pat. No. 5,949,521, U.S. Pat. No. 6,095,651, U.S. Pat. No. 6,948,818, U.S. Pat. No. 7,416,305, U.S. Pat. No. 6,595,643, U.S. Pat. No. 6,709,108, U.S. Pat. No. 6,964,480, U.S. Pat. No. 7,448,752, U.S. Pat. No. 7,419,264, U.S. Pat. No. 7,475,989, U.S. Pat. No. 6,631,991, U.S. Pat. No. 6,634,750, U.S. Pat. No. 7,226,443, and U.S. Pat. No. 7,237,898). They do not allow the end user to dynamically or partially cancel or deliberately offset some selected wavefront aberration components to thus reveal important features of other wavefront aberrations in a highlighted or pronounced manner. In addition, the traditional way to present the wavefront measurement result, generally in the form of a 2D wavefront map or Zernike polynomial coefficients is not at all easily understandable to vision correction practitioners or refractive surgeons. As such, clinical practitioners often find it difficult to interpret the wavefront measurement for guidance during the vision correction procedure to optimize the correction outcome.

In the following example embodiment are described that provide continuous real time objective feed back of the wavefront measurement in the form of a movie rather than a snap shot that is understandable to a vision correction practitioner as the vision correction procedure is on going. This enables the vision correction practitioner to dynamically offset or partially cancel only some wavefront aberration components in order to highlight or even amplify the clinically important feature(s) of the remaining wavefront aberrations that need to be further corrected. Meanwhile, wavefront measurement result needs to be presented in a manner that is easy to interpret and understand. Identification of these missed features will allow the vision correction procedure to be more easily optimized in real time.

In accordance with one or more example embodiments, the defocus component of a wavefront from an eye is offset deliberately and actively, either at the disposal of the end user or per some built-in algorithms, in response to the real time feedback and/or the display of the measured wavefront. The deliberate and active offset is used not only to serve the function of compensating the defocus of the wavefront, which can also serve the purpose of overcoming the dynamic range limit of the wavefront sensor in measuring the local tilt of a sampled subwavefront, but also to show more clearly the predominant feature(s) of other wavefront aberration component(s), thus enabling the vision correction practitioner or the refractive surgeon to fine tune the vision correction procedure and minimize the remaining wavefront aberration(s) in real time. In terms of sampling and displaying the real time wavefront measurement result, sampling around an annular ring enables one to display the local tilt of the sampled subwavefronts on a monitor in the form of a 2D centroid data point pattern, which can be fitted to a circle or an ellipse or a straight line, thus directly indicating the two major refractive errors, namely spherical and cylindrical refractive errors, as well as the axis of the cylinder/astigmatism, or fitted to a cardioid for coma or other higher order non-symmetrical forms. As a result, a refractive surgeon can easily understand the wavefront measurement result and fine tune the vision correction accordingly.

Note that of all the wavefront aberrations, the spherical refractive error generally has the largest variation range (up to perhaps ±30 diopters in some extreme cases) among different eyes, while all other wavefront aberration components such as astigmatism generally have much less variations. In addition, during a refractive surgery, if the crystal lens in the eye is removed, the aphakic eye can have a drastically different spherical refractive error diopter value than that of the phakic eye, with the difference being up to 20 diopters. Since the dynamic range of a wavefront sensor in terms of sensing the local tilt of a sampled subwavefront is limited, it is therefore desirable to arrange a defocus compensating device in the light path of the wavefront sensor to just compensate for the spherical refractive error so that the defocus compensated wavefront can be measured by the wavefront sensor. However, as mentioned before, prior art wavefront sensors with wavefront compensator(s) or adaptive optics systems basically all operate in an "on and off" format to either turn the wavefront compensation on or off. Such an operation does not provide enough help to a refractive surgeon in easily figuring out how the refractive correction should proceed in order to achieve better vision correction in real time. To overcome this shortcoming, the refractive surgeon or a built-in algorithm can selectively cancel or offset certain wavefront aberration component(s), thus enabling the remaining aberration(s) to be highlighted in a "zoomed in" or "magnified" manner. As a result, the refractive surgeon can see in real time how his/her vision correction procedure should proceed in order to remove the remaining aberration(s), confirm the results, and document the value and sense of the compensated aberrations.

Figure 5:
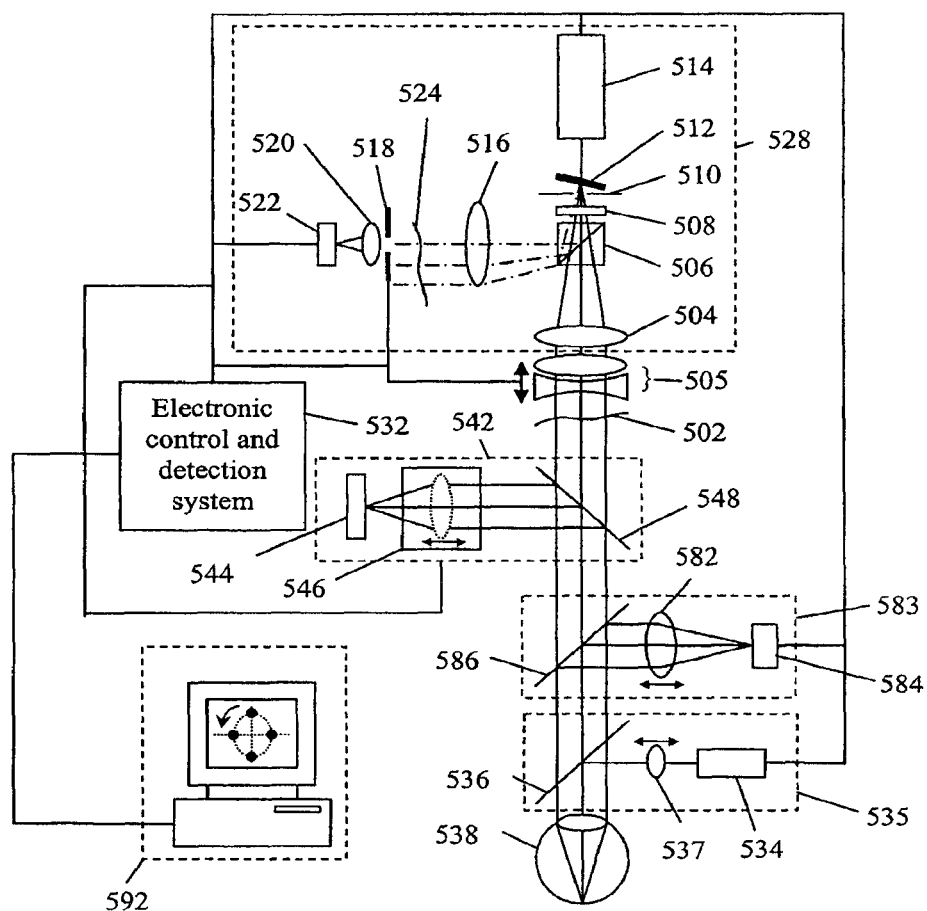
FIG. 5 shows a schematic diagram of one embodiment in which a dynamic defocus offsetting device is used to offset spherical refractive error of the wavefront from an eye.

FIG. 5 shows one embodiment of a dynamic wavefront sensing system in which a defocus offset device is used to offset the spherical refractive error component of the wavefront from an eye.

A sequential wavefront sensor 528 has a first lens 504 that focuses a linearly polarized input beam of light having a wavefront 502. The focusing beam travels through a polarization beam splitter (PBS) 506, which is arranged in such a manner that its pass-through polarization direction is aligned with the polarization direction of the incoming beam. As the result, the linearly polarized convergent beam will pass through the PBS 506. A quarter-wave plate 508 is placed behind the PBS 506 with fast axis oriented so that a circularly polarized beam is emerged after passing through the quarter-wave plate 508. A pinhole 510 is placed behind the quarter wave plate 508 and right in front of the scanning mirror 512 to serve the purpose of rejecting the light not directly coming from interested wavefront of the light beam.

The input convergent beam, after passing through the pinhole 510, is focused on the reflective surface of a tilted scanning mirror 512, which is mounted on a motor shaft 514. The light beam reflected by the mirror is divergent, with its beam central chief ray changed to a direction that is dependent on the tilting angle of the scan mirror 512 and the rotational position of the motor 514. It is expected that the reflected beam is still circularly polarized, but the circular polarization rotation direction will be changed from left hand to right hand or from right hand to left hand. Hence, upon passing through the quarter-wave plate 508 for a second time on its return path, the beam becomes linearly polarized again, but with its polarization direction rotated to an orthogonal direction with respect to that of the original incoming beam. Therefore, at the polarization beam splitter 506, the returned beam will be mostly reflected to the left as shown by the dashed light rays in FIG. 5.

A second lens 516 is placed on the left next to the PBS 506 to collimate the reflected divergent beam and to produce a replica of the original input wavefront. Due to the tilting of the scan mirror, the replicated wavefront is transversely shifted. An aperture 518 is placed behind the second lens 516 and right in front of the sub-wavefront focusing lens 520 to select a small portion of the replicated wavefront. The sub-wavefront focusing lens 520 focuses the selected sub-wavefront onto a position sensing device 522, which is used to determine the centroid of the focused light spot generated from the sequentially selected sub-wavefronts. By rotating the motor 514 and changing the tilting angle of the scan mirror 512 in a continuous or stepped fashion, the amount of radial and azimuthal shift of the replicated wavefront can be controlled such that any portion of the replicated wavefront can be selected to pass through the aperture 518 in a sequential way. As a result, the overall wavefront of the original incoming beam can be characterized as for the case of a standard Hartmann-Shack wave-front sensor with the exception that the centroid of each sub-wavefront is now obtained in a sequential rather than a parallel manner.

When the tilt angle of the scanning mirror remains constant an annular section of the wavefront 502 is sequentially scanned. The radius of the annular section can be changed by changing the tilt of the scanning mirror.

The light source module 535, comprising the light source 534, the collimating lens 537 and the beam directing element 536, is used to direct a narrow beam of light onto the retina of a patient eye 538. It has been mentioned in US20080278683 that the infrared imaging module 583 can be used to monitor the position of the fovea and also to align and register the eye. In addition, the internal fixation and visual acuity projection module 542 as shown in FIG. 5 can comprise a micro display 544, a variable focus lens 546 and a beam directing element 548, and serve the function of changing the accommodation of the patient's eye as well as checking the patient's visual acuity. When the patient's accommodative mechanism of the eye is not anaesthetized, a continuous measurement of wavefront aberrations over the full accommodation range will provide an optimized prescription for vision correction. In spite of the fact that these two modules are shown, it should also be understood that they are not absolutely required for the apparatus embodiment.

However, as one aspect of an embodiment, the internal fixation/visual acuity projection module can also be used to change the accommodation of the patient's eye with wavefront measurements also done for the whole accommodation range. During accommodation, while the axis of fixation may not change which means proper patient alignment, the actual visual axis or center may vary, indicating a kind of pseudo accommodation or non-symmetric visual correction. The wavefront sensor can record the variation and determine accommodative correction.

As another aspect of an embodiment, the internal fixation/visual acuity projection module can also be used to guide the patient to look off-axis so that the incident light beam can be guided to land on different positions of the retina rather then at the fovea region. This can be achieved by turning a certain pixel or group of pixels of the micro display 544 on and as a result, the eye will be directed to fixate on the "on" pixel(s), making it possible to capture the eye aberration wavefront for both the center and the peripheral light scattering locations. In doing so, wavefront aberrations can be measured as a function of the landing position of the incident light beam and therefore a 2D array of wavefront aberrations for light scattered from different locations on the retina can be generated. Such a 2D array of wavefront measurements will provide a vision correction practitioner with additional valuable information in addition to a conventional eye aberration wavefront measurement resulting from only a central light scattering location. This will further optimize aberration correction prescriptions in the sense that in addition to central vision, peripheral vision can also be optimized.

In FIG. 5, active defocus offsetting is achieved by changing the effective focal length or the spherical refractive power of a lens or a lens combination 505 disposed in the optical path in front of a wavefront sensor 528. The change of the effective focal length can be calibrated to indicate the correction in diopters (for example) required to change the actual wavefront returned from the retina to a plane wave. This correction in diopters is the refractive prescription for correcting the vision of a patient. The procedures for obtaining this prescription for spherical and astigmatic aberrations are described in detail below.

Note that the difference between the current embodiment and those disclosed in U.S. Pat. No. 7,445,335 and US20080278683 is that a dynamic defocus offsetting element 505 is arranged in the light path. Previous embodiments only mentioned the compensation or defocus nulling function if such an element is used. In the current embodiment, in addition to the compensation or nulling function, the defocus offsetting element 505 also provides active off-setting or partial cancellation of the spherical refractive error component in either the positive or negative direction to make the wavefront more or less spherically divergent or convergent and the active offset is at the disposal of the refractive surgeon or controlled by a built-in algorithm according to the real time display and/or feedback of the wavefront measurement.

One aspect of the embodiment is to use the defocus offset device to partially compensate for any relatively large spherical refractive error so that the remaining spherical and cylindrical refractive errors and other higher order aberrations all fall within the measurement dynamic range of the wavefront sensor. As such, the variable focal length lens is functioning as an optical component that can also substantially increase the measurement dynamic range of the combined wavefront sensing system. Another aspect of the embodiment is to scan the defocus offset within the wavefront measurement range with or without the accommodation change of the eye over the accommodation range so that a better and more precise measurement of the eye refractive errors can be obtained.

It should be noted that the defocus offsetting device described in FIG. 5 can include a set of configured lenses to allow a shifting of the focal range along the return beam optical axis. The position and axial spacing of these lenses provides an offset that can actively remove or adjust the spherical refractive error component of the transmitted beam. This active focusing alters the divergence or convergence of the beam to "fit" or allow matching of the beam focusing properties in order to accentuate other aberration properties such as the appearance of the elliptically shaped beam pattern indicating an astigmatic condition. This "fitting process" does change the spherical power of such a beam with an exact knowledge of the amount of compensatory focal change. The first order linear focal shift introduced by the offsetting active lens(es) does(do) not alter the properties of the other inherent aberrations, it serves the basic purpose of highlighting and emphasizing the underlying higher order aberrations that are present. The sensitivity to detection of the existing higher order aberrations increase with more exact fitting location as the spherical refractive error component of the aberration is "matched" or "fitted" allowing better appreciation and detection of wavefront changes imposed by the lesser slope values which can be masked by large spherical wavefront slope values.

This can be visualized by considering the appearance of the globe of the earth which has a larger base spherical shape with myriad small slope changes caused by the local terrain changes with mountain ranges being a positive local slope change and valleys being a negative slope change. If one were to flatten out the large linear spherical component of the earth the remaining lesser slope changes would become increasingly apparent as well as the better definition of the non-spheroid general elliptical shape of the globe. This active defocus offsetting acts only on the linear spherical component of the collected returned beam.

It should be noted that although a positive plus negative lens combination with relative axial movement is used as the defocus offsetting element in FIG. 5, other focus variable optical element can be used, including liquid or solid focus variable lenses, voice coil or motor driven movable lens(es), liquid crystal lens(es), acousto-optic lens(es), deformable mirror(s) and diaphragm(s). The position of the defocus offsetting element does not need to be right in front of the wavefront sensor and can be anywhere along the optical path as long as it serves the function of offsetting the defocus of the wavefront. In fact, for a compact design the defocus offsetting element can be designed together with other optical element(s) inside the wavefront sensor 528. For example, it can be combined with the front focusing lens 504 of the sequential wavefront sensor 528. Such a real time sequential wavefront can be made with a small form factor and thus be integrated into a large number of optical imaging or measurement systems, such as an eye refractive surgical microscope. It should also be noted that although a sequential wavefront sensor 528 has been illustrated in FIG. 5, other types of wavefront sensors can also be used as long as it can provide wavefront measurement, including Hartmann-Shack, Talbot-Moire, Tscherning, Ray-tracing, phase diversity and interferometric wavefront sensors.

The electronic control and detection system 532 coordinates the activation of all active elements, including the defocus offsetting device 505, the focusing lens 582 of the near infrared imaging camera 584, the accommodation changing element 546 of the internal fixation/visual acuity projector 542 and others.

Figure 6:
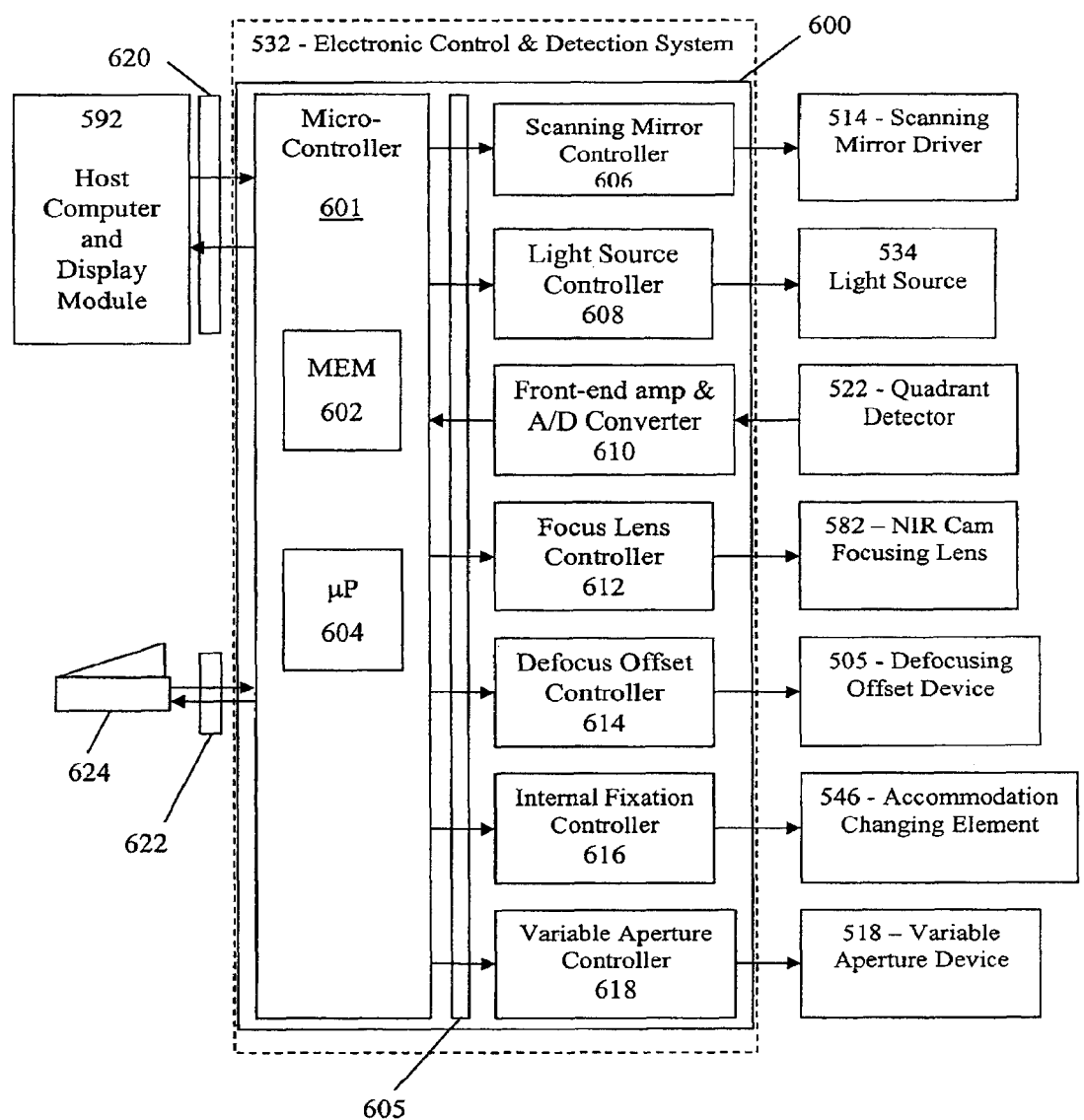
FIG. 6 shows a block diagram of a typical electronic control and detection system that is illustrated in FIG. 5.

FIG. 6 is a detailed block diagram of an example embodiment the electronic control and detection system 532. A printed circuit board (PCB) 600 includes a micro-controller 601 having a memory 602 for storing program code and data, and a processing unit 604 for executing the program code and processing the data. The microcontroller has an I/O interface (indicated by arrows) 605 coupled to various control modules 606 to 618. The control modules are interfaced with the various components of the deterministic dynamic wavefront sensing system depicted in FIG. 5 using standard techniques.

The PCB 600 also includes a host-side interface 620 for interfacing with the host computer and display module 592 and a user interface 622 for interfacing with a user interface device such as a foot pedal 624. The foot pedal can be configured to allow a surgeon to "zoom in" or "zoom out" by controlling the position of the defocusing mechanism.

The memory 602 is configured to store programs executed to perform the algorithms described below to control the deterministic dynamic wavefront sensing system depicted in FIG. 5. The various modules depicted in FIG. 6 may be implemented as discrete parts or integrated onto ASICs or other programmable devices.

The microcontroller 601 can send control signal to a scanning mirror controller connected 606 to a scanning mirror driver to drive the scanning mirror 514 and can send control signals to a light source controller 608 to turn the light source 534 on and off. Further, the microcontroller can receive signals from the quadrant detector 522 as shown in FIG. 5 through a front-end amplifier and an A/D converter 610. In addition, the microcontroller can also control the NIR camera focusing lens 582 through a focus lens controller 612. One key function of the microcontroller is to offset the defocus of the defocus offset device 505 through a defocus offset controller 614. More additional functions that the microcontroller can provide include changing the accommodation of the patient eye by controlling the accommodation changing element 546 through an internal fixation controller 616, and changing the subwavefront sampling aperture size of the variable aperture device 518 through a variable aperture controller 618. The function of the electronic control and detection sub-system can be provided by a dedicated micro-processor or a computer or other electronic processing means and therefore, the electronic control and detection system 532 shown in FIG. 5 should only be considered as an optional component but not as an absolutely needed item for the apparatus.

The display module 592 shown in FIG. 5 is included because it can be viewed directly by a refractive surgeon during a vision correction procedure to guide him/her in selecting the desired defocus offset and in optimizing the vision correction outcome. It should, however, be noted that the display module 592 in FIG. 5 should be interpreted broadly as a real time feedback means. In fact, for a vision correction surgical procedure under a surgical microscope, an approach to implement the display of the real time wavefront measurement is to incorporate a micro display inside the surgical microscope so that the wavefront measurement result can be overlaid onto the image of the patient's eye formed by the surgical microscope and presented to the refractive surgeon directly. In doing so, the surgeon does not need to move his/her head away from the binocular of the surgical microscope.

Figure 7:
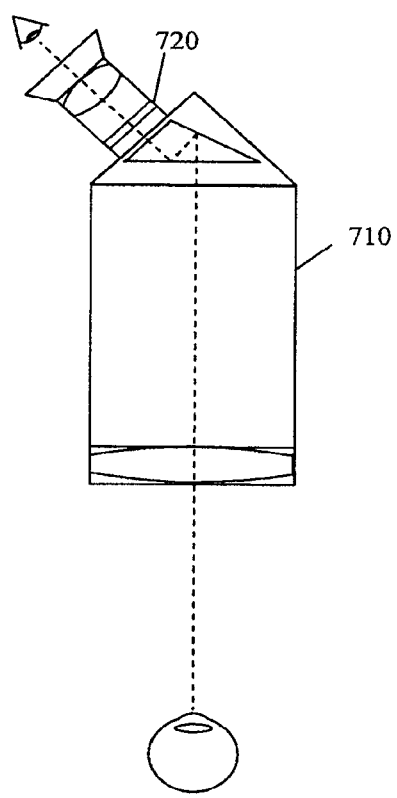
FIG. 7 shows an illustration of a surgical microscope with a micro-display incorporated at an object conjugate plane in the imaging path.

FIG. 7 shows an illustration of a surgical microscope 710 with a semi-transparent micro-display 720 incorporated at an object conjugate plane in the imaging path. This microdisplay is utilized to display the output of the deterministic dynamic wavefront sensing system of FIG. 5 so that the surgeon can respond to information provided without having to glance away from the microscope eyepiece. It should be noted that if the micro-display is not semi-transparent, a beam directing element can be arranged in the imaging path to enable the projection of the micro-display image onto the retina of a surgeon's eye. The display can also be a small LCD monitor that is mounted directly onto a surgical microscope.

On the other hand, if the surgical microscopic view is already shown on a large screen away from the surgical microscope and the surgeon is operating on the patient according to the large screen displayed microscopic view, the real time wavefront measurement result should then be preferably shown on the same large screen either as an overlaid image or separately on a different display window.

The information provided by the real time wavefront measurement with the defocus offset can also be in other data format. One example is the use of a built-in algorithm that will automatically offset or scan the defocus and at the same time inform the refractive surgeon that he/she should continue the vision correction procedure in a certain manner.

Figure 8:
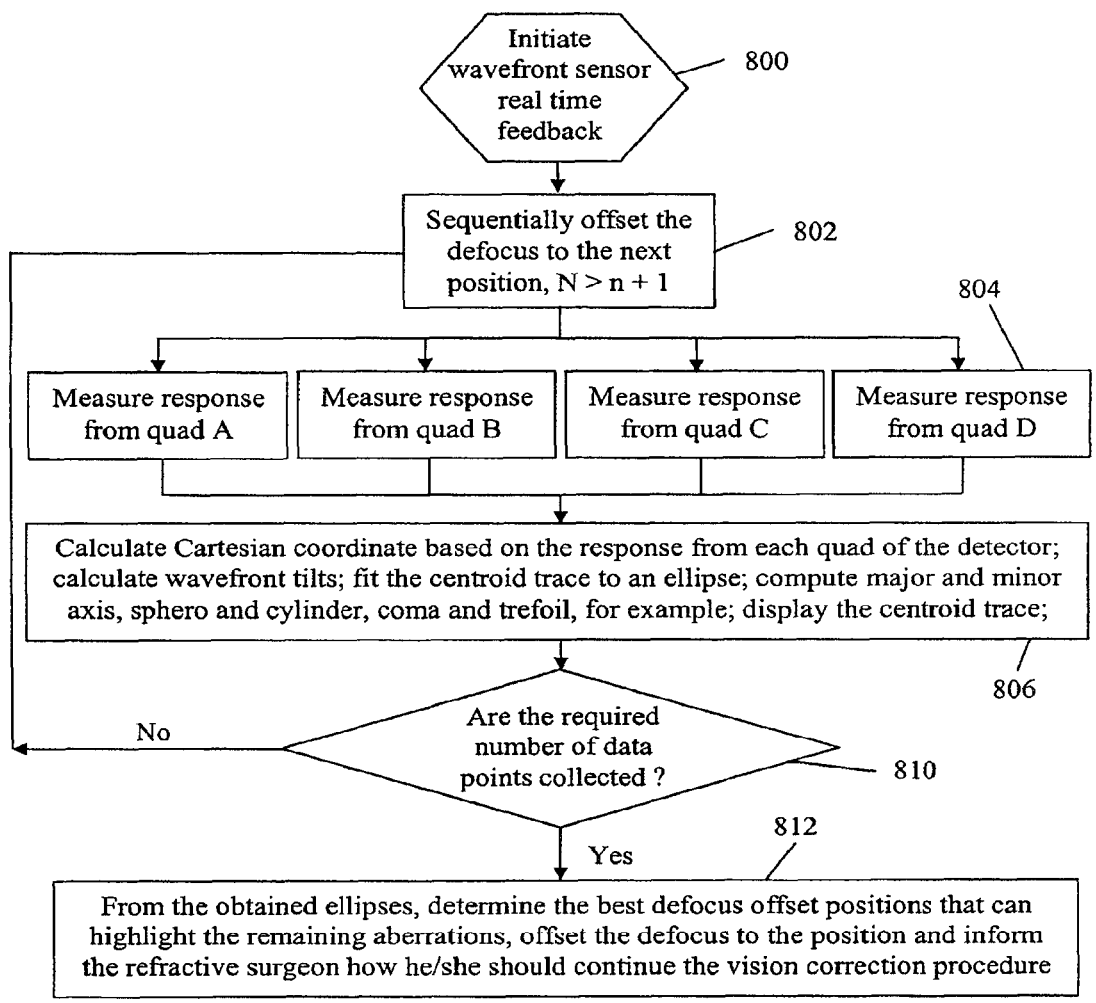
FIG. 8 shows an example flow chart of a built-in algorithm that enables the scanning of defocus to determine the best defocus offset positions that can highlight the remaining aberration(s).

FIG. 8 shows an example flow chart of such a built-in algorithm in which the defocus is scanned to determine the best defocus offset positions that can highlight the remaining aberrations. The defocus offset setting value or position is then selected and the refractive surgeon is instructed on how he/she should continue the vision correction procedure.

In process block 800 a wavefront processor real time feedback algorithm is initiated. For example, a user could select the real time feedback algorithm from a menu of algorithms displayed on the display of the host.

In process block 802 the defocus offset is moved to the next position and in process block 804 the responses from the image spot position detector quadrants are measured.

In process block 806 the Cartesian coordinates based on the response from each position detector quadrant are computed. Then, for example, wavefront tilts, the centroid locations, major and minor axes, the magnitudes of sphero, cylindrical, coma and trefoil aberrations of the sampled wavefront are determined. Also, the centroid trace is displayed. The computation can be done for the same defocus offset position a multiple number of times until for example, a desired signal to noise ratio is reached through averaging and in other words, the same annular ring can be sample a multiple number of time and averaging is done until the desired signal to noise is obtained. Also, a number of concentric annular rings can be sampled to cover the whole wavefront. In addition, the number of sub-wavefronts that one wants to sample around a single annular ring can also be changed by firing the light source in pulse mode a multiple number of times in synchronization with the scanning of the scan mirror.

In process block 810 it is determined whether the required number of defocus offset data points have been collected. If the required or desired number of data points is not reached, the processing returns to processing block 802, the defocus is offset to the next position. To determine if the required or desired number of data points is not reached or not, one can used the real time wavefront measurement result as a criterion. If the wavefront measurement indicates that the sampled sub-wavefront tilt is still within the dynamic range of the wavefront sensor, the defocus offset can continue. If the on the other hand, the wavefront sensor measurement result shows that the one or more measured sub-wavefront local tilt is already at or outside its dynamic range, this will indicate that one end of the defocus offset is reached. The same criterion can be used to determined the other end of the defocus offset until all data points within the two extremes are collected.

If the answer to the question on whether required or desired number of data points is reached is yes, then processing proceeds to processing block 812 where, from the ellipses obtained by scanning the offset, the best offset value(s) is(are) determined that can highlight remaining aberrations. This step is described in detail below with reference to FIG. 13. The defocusing mechanism is offset to one of the "best offset" values and the resulting centroid data points are displayed on a display. Information is provided to a refractive surgeon on how to best continue a vision correction procedure.

For example, the information, such as which direction to move an IOL for proper alignment or which direction to rotate a toric lens to correct astigmatism, could be provided as graphic information or text on the display.

This instruction does not have to be in a visual display format because other forms of feedback such as audio instruction can also serve the same function. In other example embodiment, the visual display module can be replaced by a general feedback mechanism which can be embedded in the electronic control and detection system 532. It is also possible that both a visual display and an audio instruction can be combined to guide the surgeon in completing the vision correction procedure.

The wavefront sensor real-time feedback algorithm can be implemented automatically by the microcontroller executing firmware held in onboard memory. Alternatively, the program code could be stored on the host and used to control the various control modules or some combination of host control and firmware could be utilized.

During a vision correction procedure, a goal is to improve the patient's vision to the point of an emmetropic state. To achieve this, low-order and high-order optical aberration errors, such as sphere, cylinder, trefoil, and coma require correction. Traditional correction occurs through a static measurement with a resultant number, typically in diopters, indicating the amount of optical refractive error and correction or nulling required. The correction is applied and another static measurement is taken to determine the effectiveness of the treatment or correction.

With the advent of presently disclosed real time wavefront measurement apparatus, not only can the dioptric values of optical aberrations be displayed real time, but an audio signal can also be provided real time to indicate the type of error, magnitude of error, and change in error. The audio feedback can consist of pitch, tone and loudness and can vary individually or collective, as examples. The audio feedback can vary high to low as the applied correction improves the error; conversely, if the applied correction worsens or adversely alters the error, the audio feedback can vary from low to high. In the advent that the user is hard of hearing, for example, the ascent and descent of the audio can be reversed.

An embodiment of audio feedback for correction of cylinder error could consist of a specific pitch identifying the error as cylinder with a tone that indicates the magnitude of the error. As the correction is applied, in this example a toric IOL is rotated, the pitch would ascend or descend (frequency would increase or decrease) whether the correction is converging toward an emmetropic state (nulling the inherent cylinder error with the IOL) or diverging. Once the desired correction is achieved a different pitch and or tone could be transmitted for confirmation or the user could listen for the transition point of ascending to descending sound.

This audio feedback, can be applied to all corrective procedures whether intraoperatively or corrective spectacles, etc. . . . . In providing this audio feedback, the clinician would not have to lift their head or divert their eyes from the correction procedure or surgery, thus minimizing potential for errors. This real time audio feedback can be applied to any application of wavefront in the detection, measurement, and/or correction of wavefront error.

It has been mentioned in U.S. Pat. No. 7,445,335 that by sampling a wavefront around an annular ring and displaying a 2D data point pattern with the location of each data point representing the local tilt in terms of centroid position of the sampled subwavefront, the centroid position 2D data point pattern can directly indicate, in real time, whether the wavefront is planer or not, how far off the defocus is, whether the defocus is convergent or divergent, what the amount of astigmatism is, and where the axis of astigmatism is.

Figure 9:
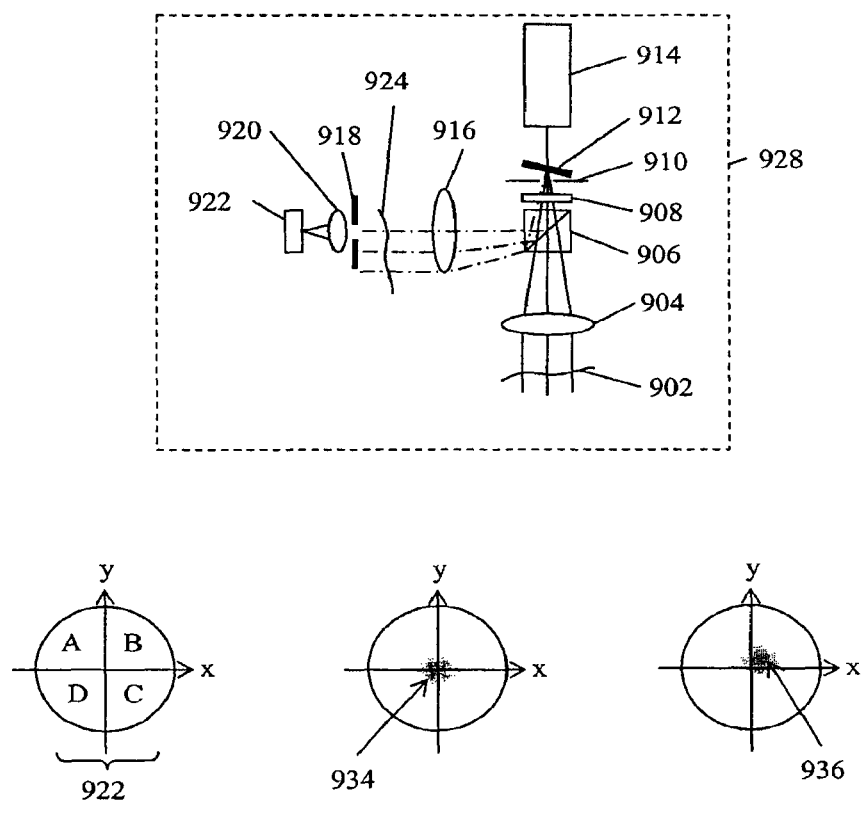
FIG. 9 shows a quad-detector with four photosensitive areas of A, B, C, and D, and the image spot on the quad-detector for a planar subwavefront and a non-planar subwavefront.

To illustrate the points, we will briefly repeat what has been discussed in U.S. Pat. No. 7,445,335. Assume that a sequential wavefront sensor 928 is used for wavefront sampling and a quad-detector 922 with four photosensitive areas of A, B, C, and D is used to indicate the local tilt in terms of the centroid position of the sampled subwavefront image spot position as shown in FIG. 9. If the subwavefront is incident at a normal angle with respect to the subwavefront focusing lens 920 in front of the quad-detector 922, the image spot 934 on the quad-detector 922 will be at the center and the four photosensitive areas will receive the same amount of light, with each area producing a signal of the same strength. On the other hand, if the subwavefront departs from normal incidence with a tilting angle (say, pointing toward the right-upper direction), the image spot on the quad-detector will then be formed away from the center (moved towards the right-upper quadrant as shown by the image spot 936).

The departure (x, y) of the centroid from the center (x=0, y=0) can be approximated to a first order using the following equation:

$$x = \frac{(B+C)-(A+D)}{A+B+C+D} \quad (1)$$
$$y = \frac{(A+B)-(C+D)}{A+B+C+D}$$

where A, B, C and D stand for the signal strength of each corresponding photosensitive area of the quad-detector and the denominator (A+B+C+D) is used to normalize the measurement so that the effect of optical source intensity fluctuation can be cancelled. It should be noted that Equation (1) is not perfectly accurate in calculating the local tilt in terms of the centroid position, but it is a good approximation. In practice, there may be a need to further correct the image spot position errors that can be induced by the equation using some mathematics and a built-in algorithm.

When a number of symmetric sub-wavefronts (for example, 4, 8 or 16) around an annular ring of an optical beam is sequentially sampled and hence projected (for example, in a clockwise direction) onto the sub-wavefront focusing lens 920 and quad-detector 922, the departure of the centroid as indicated by (x, y) of Equation (1) from the center of the quad-detector will trace a pattern on an x-y coordinate that can be displayed on a monitor and also be processed digitally to represent the status of defocus and astigmatism as well as non-symmetry.

Figure 10:
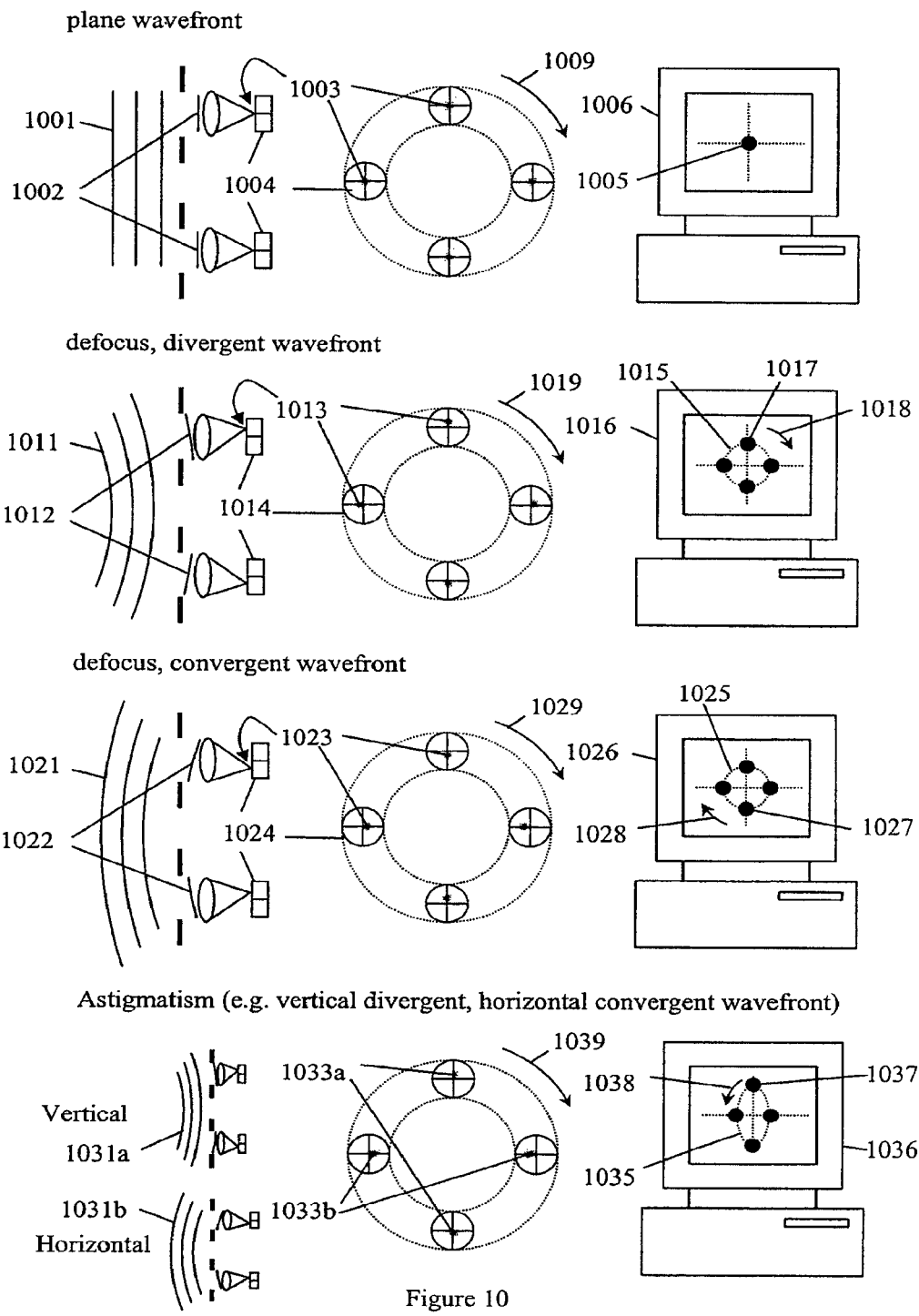
FIG. 10 shows the sampling by a sequential wavefront sensor of a number of subwavefronts around an annular ring of a planar wavefront, a wavefront with defocus and a wavefront with astigmatism, the associated image spot position on a quad-detector and the sequential movement of the corresponding centroid positions when displayed on a monitor.

FIG. 10 shows a number of representative cases of planar wavefront, defocus and astigmatism, the associated image spot position on the quad-detector behind the subwavefront focusing lens, as well as the sequential movement of the corresponding centroid positions when displayed as a 2D data point pattern on a monitor. Note that instead of drawing a number of shifted wavefronts being sampled and projected as different subwavefronts onto the same subwavefront focusing lens and the quad-detector, we have taken the equivalent representation such that a number of subwavefronts are drawn around the same annular ring and accordingly, a number of quad-detectors are drawn around the same annular ring to represent the case of scanning different portions of a wavefront to a single subwavefront focusing lens and a single quad-detector.

Assume that we start the scan around the wavefront annular ring from the top subwavefront and move in a clockwise direction to the second subwavefront on the right and so forth as indicated by the arrow 1009. It can be seen from FIG. 10 that when the wavefront is a plane wave 1001, all the subwavefronts (for example, 1002) will form an image spot 1003 at the center of the quad-detector 1004 and as a result, the centroid trace 1005 on a monitor 1006 will also be always at the origin of the x-y coordinate.

When the input wavefront is divergent as shown by 1011, the center of the image spot 1013 of each subwavefront 1012 will be on the radially outward side from the wavefront center with an equal amount of departure from the center of the quad-detector 1014, and as a result, the trace 1015 on the monitor 1016 will be a clockwise circle as indicated by the arrow 1018 starting from the top position 1017. If, on the other hand, the input wavefront is convergent as shown by 1021, the center of the image spot 1023 of each subwavefront 1022 will be on the radially inward side relative to the center of the wavefront with an equal amount of departure from the center of the quad-detector 1024. As a result, the centroid trace 1025 on the monitor 1026 will still be a circle but will start from the bottom position 1027 and will still be clockwise as indicated by the arrow 1028. Hence when a sign change for both the x-axis centroid position and the y-axis centroid position is detected, it is an indication that the input wavefront is changing from a divergent beam to a convergent beam or the other way round. Furthermore, the starting point of the centroid trace can also be used as a criterion to indicate if the input wavefront is divergent or convergent.

It can also be seen from FIG. 10 that when the input wavefront is astigmatic, it can happen that the wavefront can be divergent in the vertical direction as shown by 1031*a* and convergent in the horizontal direction as shown by 1031*b*. As a result, the centroid position of the vertical subwavefronts 1033*a* will be located radially outward with respect to the center of the input wavefront, and the centroid position of the horizontal sub-wavefronts 1033*b* will be located radially inward with respect to the center of the input wavefront. Consequently, the centroid trace 1035 on the monitor 1036 will start from the top position 1037 but move anti-clockwise as indicated by arrow 1038, hence the centroid trace rotation is now reversed.

Using a similar argument, it is not difficult to figure out that if the input wavefront is astigmatic but all the subwavefronts are either entirely divergent or entirely convergent, the rotation of the centroid trace will be clockwise (i.e. not reversed), however, for the astigmatic case, the trace of the centroid on the monitor will be elliptic rather than circular since the subwavefronts along one astigmatic axis will be more divergent or convergent than those along the other axis.

For a more general astigmatic wavefront, either the centroid trace will rotate in the reversed direction with the trace either elliptical or circular, or the centroid trace will rotate in the normal clockwise rotation direction but the trace will be elliptical. The axis of the ellipse can be in any radial direction relative to the center, which will indicate the axis of the astigmatism. In such a case, 4 subwavefronts around an annular ring may not be enough in precisely determining the axis of the astigmatism and more subwavefronts (such as 8, 16 or 32 instead of 4) can be sampled around an annular ring.

As mentioned in the summary section, one novel feature of the embodiments is the way the wavefront is sampled and the wavefront measurement result is displayed. Although in U.S. Pat. No. 7,445,335, it has been mentioned that by sampling a number of subwavefronts around an annular ring of the wavefront from a patient's eye, the spherical and cylindrical refractive errors (or defocus and astigmatism) of the eye can be determined, there was no detailed explanation about the effect of actively offsetting the defocus on the 2D data point pattern. If the eye has a relatively large spherical refractive error and a relatively small astigmatism, the 2D centroid data point pattern will look more like a circle with its ellipticity hardly visible and this will make it hard to detect the axis of the astigmatism as well as the amount of the astigmatism. On the other hand, if the defocus of the original wavefront has a proper offset, the remaining astigmatism can be made to clearly show itself up in the 2D data point pattern, clearly indicating the axis and the amount of the astigmatic error.

Figure 11:
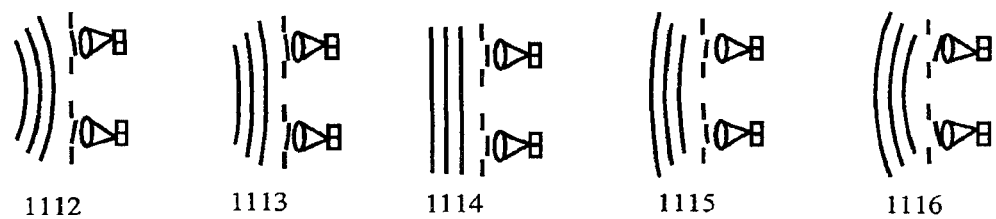
FIG. 11 shows the cross sectional wavefronts with different defocus offset and the corresponding change of the 2D centroid data point pattern for the case of an eye with only defocus or spherical refractive error.
Figure 11:
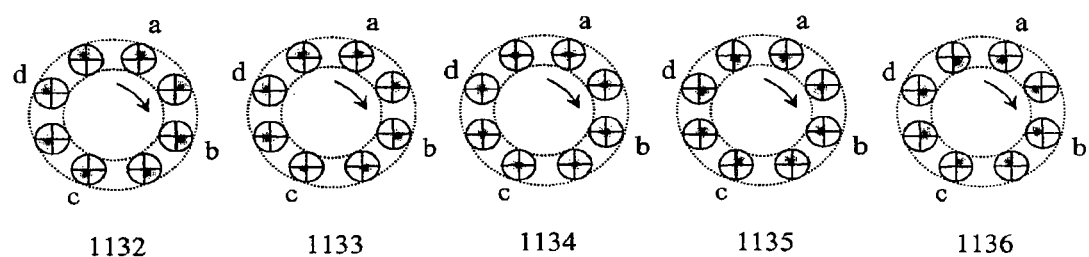
Figure 11:
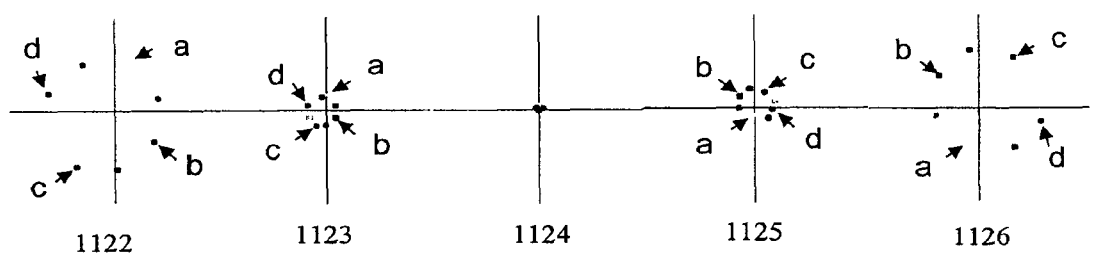

FIG. 11 shows the meridianal cross sections of the wavefront with different defocus offset and the corresponding change of the 2D data point pattern for the case of an emmetropic eye or an eye with only spherical refractive error. In FIG. 11 a top row of wavefront drawings 1112 to 1116 depicts the curvature of the wavefront for a particular defocus offset and the part of the detector upon which an image spot of the sub-wavefront is focused by a lens. A middle row of drawings shows a ring of detectors oriented to detect the focused image spot of sub-wavefronts of an annular portion of the wavefront and the offsets of the wavefront centroids from the center (x=0, y=0) of the detectors. A bottom row depicts the departure of each centroid on each detector quadrant displayed relative to an origin corresponding to (x=0, y=0). The letter labels on the displayed data points of the display correspond to the labels of the detectors in the ring of detectors.

In FIG. 11, the wavefront illustration, detector illustration and display illustration for a single defocus offset are arranged vertically. For example, for the defocus offset 1112, the detectors and image spots are depicted in 1132 and the display in 1122.

It can be seen that as the defocus offset is tuned (from left to right), the resultant wavefront will change from a spherically more divergent wavefront 1112, to a spherically less divergent wavefront 1113, to a planar wavefront 1114, to a spherically less convergent wavefront 1115, and to a spherically more convergent wavefront 1116. Correspondingly, the image spot position on quad-detector will also change as shown in FIG. 11 from radially more outward 1132, to radially less outward 1133, to landing at the center 1134, to radially less inward 1135, to radially more inward 1136. In accordance, the 2D data point pattern will also change from a larger circle 1122 with data point "a" at the first quadrant, to a smaller circle 1123 with data point "a" still at the first quadrant, to a centered collection of the data points 1124, to a smaller circle 1125 with data point "a" now at the third quadrant, and then to a larger circle 1126 with data point "a" still at the third quadrant.

One feature associated with sequential sampling of the subwavefronts around an annular ring is that, regardless of whether the resultant wavefront is spherically divergent or convergent, the sequence of the 2D data points displayed will follow a certain rotation direction (as shown by the sequence of a, b, c, d in FIG. 11). However, the position of the data points will be on the opposite side of the circular centroid trace if there is a change in the divergence or convergence of the spherical wavefront. Therefore the location of the data points relative to the center of the circle can tell if the wavefront is divergent or convergent.

As one aspect of an embodiment, a calibration wavefront measurement can be made for a substantially planar wavefront to determine the relationship between the centroid trace diameter, the annular ring diameter and/or width, and the defocus offset. Then a real measurement of a wavefront from an eye can be made by scanning the defocus offset, also possibly the annular ring size in terms of its diameter and width, and relating the measurement results to the calibration data. In doing so, a more accurate measurement of the spherical refractive error of an eye can be obtained.

Additionally, FIG. 11 actually also shows a phenomenon that can be used for alignment. Note that the center of the 2D data point pattern or centroid trace circle actually moved as the defocus offsetting element is scanned. This can be caused by a misalignment of the optical axis between the wavefront sensor and the defocus offsetting element, or it can be caused by a lateral or transverse movement of the eye when the defocus offsetting element is tuned or scanned. Therefore, as one aspect of an embodiment, this phenomenon can be used to align the defocus offsetting device with the wavefront sensor. As another aspect of an embodiment, the real time wavefront sensor with active defocus offsetting element can also be used to indicate the alignment of the eye relative to the presently disclosed apparatus.

In addition, the apparatus can also be used with the real time display of the 2D data point pattern to guide the end user in aligning the patient's eye with the apparatus. Furthermore, it can also be used for eye tracking. The defocus offset can be properly selected so that a desired 2D data point pattern with a proper dimension can be obtained and a built-in algorithm can be used to extract the center position of the 2D data point pattern and drive a mechanical mechanism to move the apparatus relative to the patient eye in a closed loop fashion so that the eye is always aligned with the apparatus. Another aspect of this feedback position for alignment is to implement a real time correcting algorithm that updates the data with respect to correcting the shifted coordinates measured and actively displays the properly aligned data.

It should be noted that although in FIGS. 9, 10, and 11, the origin of the x-y coordinate is used as the reference point. This is only one special case. In fact, if the quad-detector is not axially aligned with the optical axis of the subwavefront focusing lens, the image spot of a planar subwavefront will not be equally shared by the 4 quadrants. If, in this case, the overall wavefront is planar, all the sample subwavefronts will still be planar and hence all the centroid data point location will be the same. In other words, when the overall wavefront is planar, the 2D centroid data points will collapse to the same position which does not need to be the origin of the x-y coordinates. So a practical approach for alignment of the patient eye or the defocus offset device relative to the wavefront sensor is to use a reference planar wavefront to identify this reference point on the x-y coordinate and then to use a built-in algorithm to indicate if the measured wavefront, either from the patient eye or after passing through some optical element such as the defocus offsetting device, is aligned relative to this reference point FIG. 12 shows, for the case of an eye with both defocus and astigmatism, the vertical and horizontal cross sectional wavefronts with different defocus offsets, the corresponding image spots of the sampled subwavefront on the quad detector, and the corresponding change of the 2D data point pattern.

Figure 12:
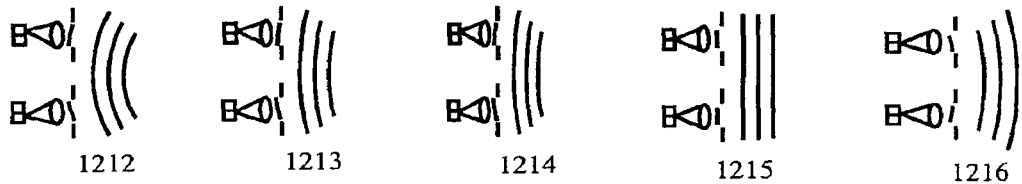
FIG. 12 shows respectively the vertical and horizontal cross sectional wavefronts with different defocus offset, and the corresponding change of the 2D centroid data point pattern for the case of an eye with both defocus and astigmatism.
Figure 12:
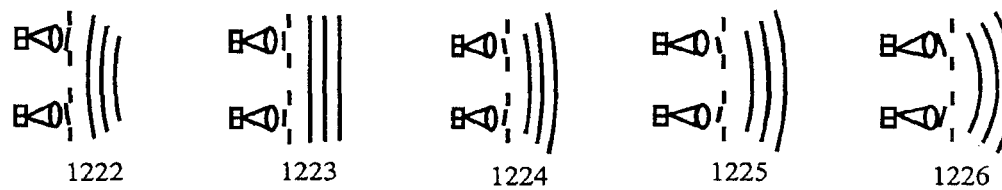
Figure 12:
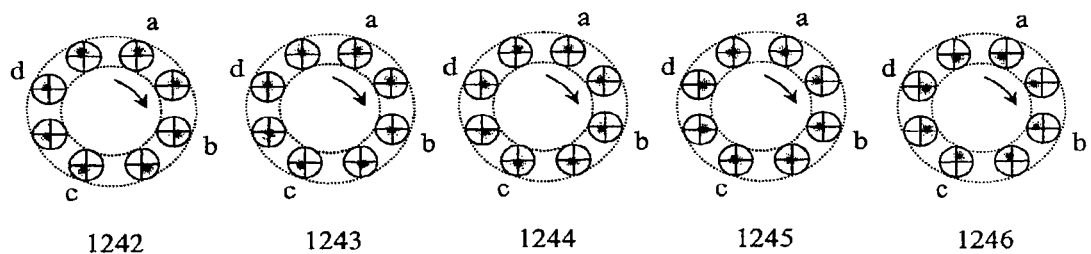
Figure 12:
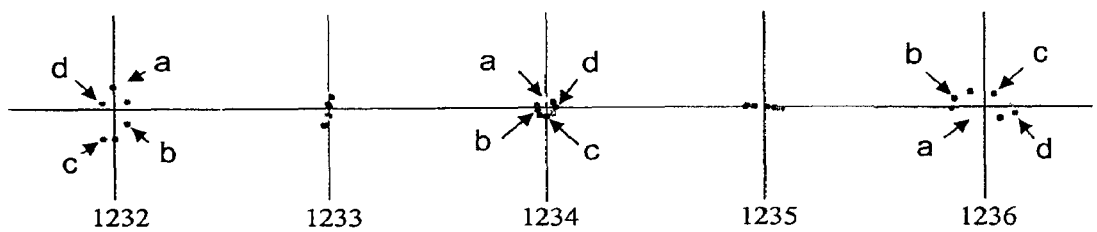
Figure 12:
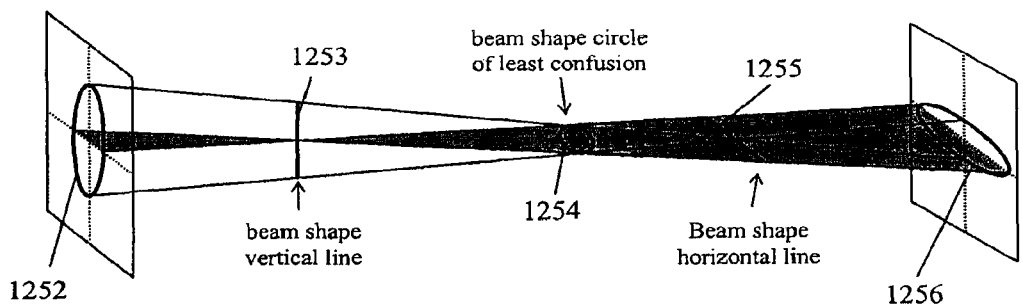

FIG. 12 is organized the same as FIG. 11 except that vertical and horizontal sections of the wavefront are now depicted because in the case of astigmatism those sections will have different curvatures as described above with reference to FIG. 4.

As described above, the Axis of astigmatism is a number anywhere between 0 and 180 degrees; this axis number tells where the difference in corneal curvature occurs or how the astigmatism is oriented or aligned. In both FIG. 4 and FIG. 12 the Axis is either a vertical line or a horizontal line to facilitate clear description. However, as known in the art, the axis can have other values for the actual eye being measured.

As the defocus offset is tuned as shown in FIG. 12 (from left to right), the vertical cross sectional wavefront 1212 is initially more divergent than the corresponding horizontal cross sectional wavefront. Correspondingly, the image spots on quad-detector as shown by 1242 will be more radially outward for those subwavefronts sampled at the top and bottom portion of an annular ring (a and c) than those sampled at the left and right portion of the annular ring (d and b). As a result, the 2D centroid data point pattern 1232 will be an ellipse with the major axis aligned substantially vertically.

With the defocus offset tuned further, the vertical cross sectional wavefront 1213 becomes less divergent while the corresponding horizontal cross sectional wavefront 1223 is planar. Therefore, the image spots on quad-detector as shown by 1243 will be less radially outward for those subwavefronts sampled at the top and bottom portion of an annular ring (a and c), while the image spots of those subwavefronts sampled at the left and right portion of the annular ring (d and b) will land substantially close to the center of the quad-detector. As a result, the 2D centroid data point pattern 1233 will substantially resemble a vertical line.

With the defocus offset tuned further, the vertical cross sectional wavefront 1214 can become even less divergent with a degree of divergence that is equal to the degree of convergence of the horizontal cross sectional wavefront 1224 that has passed the planar wavefront point and changed from divergence to convergence. Correspondingly, the image spots on quad-detector (a and c) as shown by 1244 will be even less radially outward for those subwavefronts sampled at the top and bottom portion of an annular ring while those image spots for subwavefronts sampled at the left and right portion of the annular ring (b and d) will now be somewhat radially inward with the inwardness equal to the outwardness of the image spots of those subwavefronts sampled at the top and bottom portion. As a result, the 2D centroid data point pattern 1234 will resemble a circle with reversed rotation sequence as discussed before.

With the defocus offset still tuned further, the vertical cross sectional wavefront 1215 now becomes planar while the horizontal cross sectional wavefront 1225 becomes more convergent. Correspondingly, the image spots on quad-detector as shown by 1245 will land close to the center for those subwavefronts sampled at the top and bottom portion of an annular ring (a and c) while for those subwavefronts sampled at the left and right portion of the annular ring (b and d) the image spots will be more radially inward. As a result, the 2D centroid data point pattern 1235 will resemble a horizontal line.

With the defocus offset tuned even further, the vertical cross sectional wavefront 1216 will have passed the planar point to become slightly convergent while the horizontal cross sectional wavefront 1226 now becomes even more convergent. Correspondingly, the image spots on quad-detector as shown by 1246 will be radially slightly inward for those subwavefronts sampled at the top and bottom portion of an annular ring (a and c) while for those sampled at the left and right portion of the annular ring (b and d) the image spots will be even more radially inward. As a result, the 2D centroid data point pattern 1236 will resemble a horizontal ellipse.

It can be seen from FIG. 12 that when the degree of ellipticity is small, it will be more difficult to precisely determine the major and minor axis of the ellipse and the amount of ellipticity both of which relate to the astigmatic refractive error. Similar to the pure defocus or spherical refractive error case, the sequence of the 2D data point pattern, although now resembling an ellipse, will follow a certain rotation direction if the subwavefronts are sampled sequentially around an annular ring. Again, the location of each data point will be on the opposite side relative to the center of the ellipse if there is a change in the overall divergence or convergence of the resultant wavefront. So if the rotation of the centroid trace is not reversed, the location of the data points relative to the center of the ellipse can tell if the overall wavefront is divergent or convergent. Meanwhile the shape of the ellipse in terms of the major and minor axis orientation, the major and minor axis length and the ratio of the major axis length over the minor axis length or the ellipticity can all be used to tell the degree of the measured astigmatism.

However, when the defocus offset is tuned towards a better compensation of the defocus component, the resultant wavefront will change in such a way that the overall divergence or convergence will decrease until along a particular direction on the resultant wavefront, the local tilt becomes zero i.e. the associated cross sectional wavefront becomes planar as shown by 1223 and 1215. The corresponding two straight lines of the 2D centroid data point patterns (1233 and 1235) will be perpendicular to each other if there are no higher order aberrations except for defocus and astigmatism. As the defocus offsetting device is further tuned towards an even better compensation of the defocus component, the result wavefront will have a larger portion more divergent and a smaller portion less convergent or the other way round. The 2D data point patterns for such a case are not shown in FIG. 12, but it can be envisioned based on our discussion made so far. One feature of the 2D data point pattern for now is that the sequential rotation of the centroid trace will be reversed and the data point pattern will resemble a smaller ellipse with a shorter major axis. Again the shape of the sequentially reversed ellipse in terms of the major and minor axis orientation, the major and minor axis length and the ratio of the major axis length over the minor axis length or the ellipticity can all be used to tell the degree of the measured astigmatism.

When a substantially good compensation of the sphero defocus component occurs, the resultant wavefront is equally divergent for half of the overall wavefront (1214) and equally convergent for the other half of the overall wavefront (1224). The sequential rotation of the now circular 2D data point centroid trace will be reversed as compared to that of the two large ellipses 1232 and 1236.

It is worth mentioning that although there is a difference between the 2D centroid data point pattern as the defocus offset is tuned or scanned around the "best focus" region and the cross sectional shape of a beam with astigmatism that is being focused, the fact is, there is actually a very good correspondence and similarity between the two. This very similar behavior is a key feature of the present disclosure that makes the presentation of the wavefront measurement result so easy for vision correction practitioners to understand. Let us assume that a beam derived from a point source near the fovea is coming out from an eye that has nearsightedness and also astigmatism and that the beam gets focused from right to left as shown at the bottom portion of FIG. 12. After leaving the eye, the beam will gets focused sooner in the vertical direction than in the horizontal direction. This will make the beam cross section shape resemble a horizontal ellipse 1256.

At this moment, it should be reminded again that there is a difference between geometric ray optics which is an approximation and wave optics which is more accurate, in the sense that ray optics as shown in FIGS. 2 and 4 assumes that a beam can be focused to an infinitely small size so the curvature of a spherical wavefront will not change which is not true, but in reality, wave optics shows that as a convergent beam gets focused, the wavefront will gradually transform from being convergent with a relatively fixed radius of curvature as predicted by ray optics, to being more convergent, to being less convergent, to being planar and then to being less divergent, being more divergent and finally to being less divergent with a relatively fixed radius of curvature as predicted by ray optics. Accordingly during the transition, the radius of curvature of the wavefront will change from positively larger but more constant as predicted by ray optics to smaller to larger, to infinity, and to negatively larger to smaller to larger but with a relatively fixed radius of curvature as predicted by ray optics. Note that in FIG. 12, we are only presenting the case for the region near "best focus" which is not the ray optics theory still valid region.

So if we look at the vertical cross sectional wavefront, as it gets closer to its "best focus" position, it will become less convergent sooner than the horizontal cross sectional wavefront that is still far from its "best focus" position. This wavefront situation corresponds to 1216 and 1226. It happens that the 2D data point pattern 1246 is also a horizontal ellipse so there is a good correspondence.

As the astigmatic beam gets more focused, it becomes a horizontal line 1255. This means that in the vertical direction, the beam is best focused. So the vertical cross sectional wavefront should be planar (1215) while the horizontal cross sectional wavefront is still convergent (1225). Note that the 2D centroid data point pattern 1235 is also a horizontal line, so again there is a good correspondence.

As the astigmatic focusing beam propagates further, it turns into a circle of least confusion and the beam shape will be a circle 1254. At this location, the vertical cross sectional wavefront will have passed the planar location and is becoming slightly divergent (1214), while the horizontal cross sectional wavefront is still slightly convergent (1224) because it has not reached its "best focus" position. Correspondingly, there is a sequentially reversed circular 2D data point pattern 1234.

As the astigmatic focusing beam travels further, the beam shape becomes a vertical line 1253. Note that the vertical cross sectional wavefront now becomes more divergent (1213) while beam get perfectly focused in the horizontal direction which means that the horizontal cross sectional wavefront is planer (1223). Correspondingly, the 2D centroid data point pattern is also a vertical line 1233.

With the astigmatic focusing beam propagating even further, the beam shape turns into a vertical ellipse (1252). At this position, the vertical cross sectional wavefront becomes even more divergent (1212) while the horizontal cross sectional wavefront is just becoming slightly divergent (1222). It happens that the 2D data point pattern is also a vertical ellipse (1232).

Combining the above discussion with that made for a spherically convergent or divergent wavefront beam being focused and a planar wavefront beam, it can be seen that the goal of getting the 2D data point pattern to collapse together is also a good correspondence to focusing a beam to a single point. So the 2D centroid data point pattern obtained from a wavefront measurement by sampling around an annular ring of the wavefront of a beam can intuitively indicate the state of emmetropia and the existence of spherical and cylindrical refractive errors in a manner that can be so easily understood by vision correction practitioners. So it should be understood that the unique way of presenting a wavefront measurement in the form of a 2D centroid data point pattern that has the similar properties as the shape of a beam being focused is a key feature of an embodiment of the present disclosure.

As one aspect of an embodiment, a calibration wavefront measurement can be made for a substantially planar wavefront to determine the relationship between the centroid trace parameters, the annular ring diameter and width, and the defocus offset. Then a real measurement of a wavefront from an eye can be made by scanning the defocus offset, and also possibly the annular ring size in terms of its diameter and width, and relating the measurement results to the calibration data. In doing so, a more accurate measurement of both the spherical refractive error and the cylindrical refractive error of an eye can be obtained.

Note that the same eye or optical element alignment and eye tracking concept that has been discussed for the spherical refractive error case can still be applied to an eye with both spherical and cylindrical refractive errors. In this case, as the defocus offsetting device is scanned, the center of the ellipse (with the straight lines and the sequentially reverse circle as the extreme case of an ellipse) can be compared to the reference point and if the centers always land to within a predetermined distance from the reference point, it can be considered that good alignment or tracking has been achieved.

It should be noted that if the eye has higher order aberrations other than or in addition to defocus and astigmatism, the 2D data point pattern will depart from an ellipse (with the circle and the straight line being two extreme cases of an ellipse). As one aspect of an embodiment, such a non-perfect elliptical data point pattern or centroid trace can be either displayed directly or fitted to an ellipse and the drifting off of the data points from a fitted ellipse will indicate to the vision correction practitioner that there are higher order aberrations. The amount of non-symmetric drift or variance from the best fit ellipse can be used to assess the best nulled focus location with optimal measurement of spherical nulling. This form of displaying higher order aberrations will obviously be more acceptable and understandable to a vision correction practitioner than a 2D wavefront map or Zernike polynomial coefficients. It should be noted, however, that when non-symmetry is shown in the display, it can means a number of possible causes. For example, it can be caused by a misalignment of the eye relative to the presently disclosed apparatus. Under such a circumstance, the actual spherical refractive error induced centroid pattern will most likely not be symmetric and symmetry should not be forced by alignment away from axis of fixation as otherwise incorrect astigmatism will be reported.

The most interesting feature about the two defocus offsets that result in the two straight line shape of the 2D data point pattern is that the line can more clearly show the axis of the astigmatism. Meanwhile the length of the straight lines combined with the amount of defocus can directly indicate the degree or diopter value of the astigmatism. Although the length of the straight line is dependent on the annular ring diameter or radius, and also to a certain extent, on the sampling aperture size, but these can be determined and calibrated in advance. As one aspect of an embodiment, the defocus offsetting device can be scanned to find the two straight lines of the 2D data point patterns, such a scanning can be initiated by the vision correction practitioner or the refractive surgeon or by a built-in algorithm, and the defocus offset can be stopped at one of the two values or positions to show the straight line on the display. The defocus scanning will enable the end user to achieve a more precise determination of the axis and amount of astigmatism. The scanning of the defocus, and also possibly combined with the scanning of the annular ring, can also serve the purpose of averaging out noise and obtaining a better measurement of the aberration of the eye. For example, the range between the two defocus offset values that induce the two straight lines for the 2D data point pattern can be used to provide information about the astigmatism of the eye.

The two straight lines of the 2D data point pattern actually show that one can correct the refractive errors using at least two combinations of spherical and cylindrical lenses. The first combination is to use the defocus offset value that resulted in the first (vertical) straight line 1233 to select a spherical lens to correct the spherical refractive error. Such a spherical lens will make the horizontal cross sectional wavefront 1223 planar. At the same time, since the vertical cross sectional wavefront 1213 is still slightly divergent, a positive cylindrical lens can be used to only focus light in the vertical direction (more generally, the direction along the first straight line) to bring the vertically still slightly divergent wavefront to planar wavefront. As a result, the 2D centroid data points can all be brought to the center and the overcall wavefront can be made completely planar. This will lead to a perfect correction of the spherical and cylindrical refractive errors.

The second combination is to use the defocus offset value that resulted in the second (horizontal) straight line 1235 of the 2D centroid data point pattern to select a spherical lens to correct the spherical refractive error. Such a spherical lens will make vertical cross sectional wavefront 1215 planar. At the same time, since the horizontal cross sectional wavefront 1225 is slightly convergent, a negative cylindrical lens can be used to only negatively focus light in the horizontal direction (more generally, the direction along the second straight line) to make the horizontally slightly convergent wavefront to planar wavefront. As a result, the 2D centroid data points can all be brought to the center and the overcall wavefront can be made completely planar. This will lead to another perfect correction of the spherical and cylindrical refractive errors.

Besides these two combinations, there are also other combination possibilities. For example, if the defocus (spherical lens) correction corresponds substantially to the circle of least confusion case which is somewhere between the two straight lines, then the astigmatic correction would require a cylindrical lens with both positive and negative cylinder refractions respectively at two orthogonal orientation directions. It is perhaps more practical to choose a thinner overall lens combination that corresponds to smaller diopter values for both the defocus correction and the astigmatism correction. In some cases, the spherical correction can be that which corresponds to the circle of least confusion. To achieve this, the defocus offset can be scanned and a built-in algorithm can be used to find the best fit to a sequentially reversed circular 2D data point pattern by matching the length of the major and the minor axis. This defocus offset will then be the expected spherical correction and the diameter of the 2D data point pattern circle can be used to determine the degree of the still remaining astigmatism for the selection of a cylindrical lens with both positive and negative but orientation-wise orthogonal focusing powers.

Note that dynamically offsetting the defocus based on the real time wavefront measurement feedback will provide many advantages for eye aberration measurement and vision correction. As an embodiment, when the disclosed apparatus is used for determining the refractive errors of a patient's eye, the end user can enable the apparatus to scan the defocus offsetting device and also change the patient's accommodation to obtain a more precise measurement of the refractive errors under different accommodation conditions. Changing the accommodation to find out the patient accommodation range will enable the doctor to identify the range and also the far side of the accommodation and hence make the patient to fixate at a desired distance. Then the desired spherical and cylindrical refractive corrections or even higher order aberration correction prescription can be made based on the series of 2D data point centroid patterns, such as one of the two 2D data point pattern straight lines, obtained by scanning the defocus.

A prescription can also be generated automatically using a built-in algorithm that takes advantage of the scanning of the defocus and also the accommodation. For example, the defocus offset device can be firstly briefly scanned to identify and assume an offset value that will enable wavefront to be measured from a patient to fall within the wavefront sensor measurement range. Afterwards, the accommodation range of the eye can be determined by scanning the internal fixation while the wavefront sensor is monitoring the wavefront change. Within the accommodation range, as the internal fixation is scanned, the eye will be able to compensate so the measured real time wavefront will tend to restore to the same state. However, when the internal fixation is scanned to the one of the two accommodation limits, the eye will no longer be able to compensate for the internal fixation change, the eye is now "fogged". Any further internal fixation scanning will render the eye not responding and the real time wavefront measurement will show that the eye has reached one of the two accommodation limits. In this way the two limits of the eye's accommodation can be found. These processes can be run automatically by a built-in algorithm.

Following the determination of the accommodation range, the eye can be made to fixate at far side of the accommodation limit. Then the defocus offsetting device can be scanned to identify, for example, one of the two 2D centroid data point pattern straight lines. Again, this can be done automatically by a built-in algorithm. Since there is a pre-calibration, the length of the straight line and the orientation direction will be able to provide a prescription of the cylindrical lens and the current defocus offset value should be able to provide a prescription of the spherical lens. The thus obtained lens prescription has considered the accommodation range and will enable the patient to see a distance object clearly and at the same time also be able to focus to clearly see an object that is as near as his accommodation range allows.

The prescription can be tested on the patient using trial lenses. Again, the patient's accommodation can be changed and the real time display of the 2D data point pattern will tell the end user if the vision correction is good or not. In addition, with the precision of a wavefront measurement around different annular ring sizes and also with a control of the patient accommodation along the full accommodation range, it is highly likely that the prescription thus obtained (that could have also considered higher order aberrations) will be far more accurate than what can be obtained using a simple autorefractor, and therefore, there is a possibility that such a prescription will be good enough to make the subjective confirmation no longer necessary.

As another aspect of an embodiment, a digital processor with a built-in algorithm can be used to calculate and show the centration, the magnitude or the length as well as the orientation direction of angular axis of the major and minor axes of the best fitted ellipse on the display, thus directly telling the end user the spherical and cylindrical refractive errors of the wavefront being measured. The digital processor can also perform a best fit of the displayed 2D data point pattern to an ellipse and further guide the end user in fine tuning the defocus offset so that an even more precise determination of the astigmatic axis can be achieved.

Figure 13:
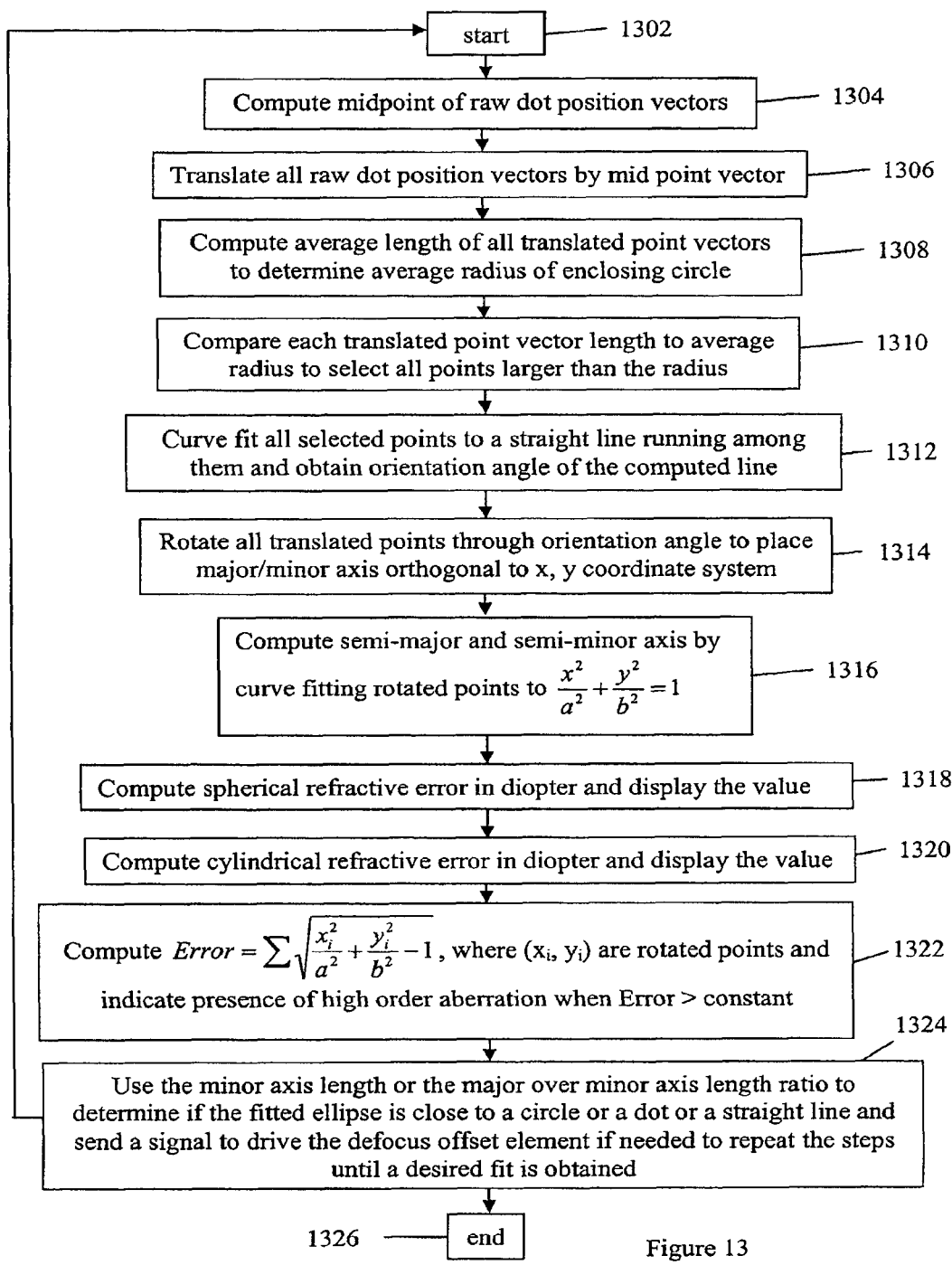
FIG. 13 shows an example flow chart of the major steps in finding the major and minor axis, and thus the spherical and cylindrical refractive errors of the measured wavefront based on the 2D centroid data point pattern.

FIG. 13 shows an example flow chart of the major steps in finding the major and minor axis and the spherical and cylindrical refractive errors of the measured wavefront based on the 2D centroid data point pattern. As an option, the processor can also indicate the presence of higher order aberrations relative to a predetermined criterion. The processor can generate a signal to show the departure of the fitted ellipse to a circle or a collection of data points or a straight line and this signal can be used to drive the wavefront offsetting element or device. The information obtained can be displayed together with 2D centroid data point pattern in the wavefront display window. For example, at one corner of the wavefront display window, real time refractive errors in terms of the sphero-cylindrical diopter values and the astigmatism axis in degrees can be displayed together with the major and minor axis length of the best fit ellipse, the ratio of the two axis, and the presence or absence of high order aberrations. In addition, during a vision correction procedure, the real time information displayed can be automatically digitally "zoomed out" or "zoomed in" to alert the vision correction practitioner that the correction is going in the wrong or right direction. When a certain level of correction has been reached, the displayed information can turn into a highlighted form in terms of, for example, font size, boldness, style or color.

Processing starts in process block 1302 and proceeds to block 1304 where the midpoint vector of the raw data point position vectors returned from the position sensors is computed. In processing block 1306 all the raw data point position vectors are translated by the midpoint vector. In process block 1308 the average length of the translated point vectors is computed to determine the average radius of an enclosing circle. In processing step 1310 each translated point vector length is compared to the average radius to select all point vectors having a vector length larger than the selected radius.

In processing step 1313 a curve fitting algorithm is used to determine an orientation angle of a straight line that best fits the selected point vectors. This angle is one of the axes of astigmatism. In process step 1314 all translated points are rotated by the orientation angle to place the major and minor axes orthogonal to an x,y coordinate system.

In process step 1316 the magnitudes of semi-major and semi minor axes are determined by curve fitting the rotated point vectors to the formula for an ellipse. In process steps 1318 and 1320 the magnitudes of the semi-major and semi-minor axes are used to compute the spherical and cylindrical refractive errors in diopters. As described above, this information is provided to the user as a prescription for corrective lenses.

In process step 1322 the error from an ellipse is calculated to indicate the presence of higher order aberrations which can be further analyzed to determine corrective measures.

In process step 1324, the minor axis length or the major over minor axis length ratio of the fitted ellipse can be used to determine if the fitted ellipse is close to circle or a data point or a straight line and a signal can be outputted to drive the wavefront offset element to change the offset. Per a built-in algorithm or the input from the end user, the process steps can be repeated until a desired fit to for example a straight line is obtained. Finally, the process ends at process step 1326.

The algorithm can be implemented automatically by the microcontroller executing firmware held in onboard memory. Alternatively, the program code could be stored on the host and used to control the various control modules or some combination of host control and firmware could be utilized.

The displayed 2D data point pattern can also be digitally "zoomed in" or "zoomed out" to "magnify" or "de-magnify" the 2D data point pattern on the display. This feature will be extremely useful for a real time vision correction procedure. The scanning of the defocus offset will enable the end user to find the two "straight lines" and hence the axis of the astigmatism. In conducting a real time correction of the astigmatism, the length of the two "straight lines" or the length of the ellipse will shorten as the correction is being performed and at a certain stage, there will be a need to "zoom in" and fine tune the defocus offset to see if the 2D data point pattern still resembles a "straight line", until its disappearance and the achievement of a "perfect" circle or the complete clustering together of the data points.

The presently disclosed apparatus can be designed for ease of operation in several ways in terms of user interaction with the apparatus. First, patient demographic information can be entered into the system. This occurs either by direct input of data through a computer keyboard, or via established communication and security standards such as DICOM and HIPAA compliant services to an Electronic Medical Record that connects via an electronic network and communicates with an established interface such as Health Language 7. Once the patient demographics are loaded into the device, a number of other parameters are selected. Any of the inputs from the user can be performed by a variety of paradigms, including keyboard, touch screen, voice, virtual reality gloves, and footswitch. The parameters that can be entered initially include operative eye, procedure being performed (e.g. toric, multifocal, or accommodating intraocular lens [IOL] implantation), cylinder to display in plus or minus configuration, recording of data on/off, audio feedback on/off, and heads-up display on/off.

Once the above information has been entered, the system is ready to begin use. The surgeon then completes the cataract extraction, and prior to IOL insertion, begins measuring the aphakic eye's wavefront. The deterministic dynamic wavefront sensing system is turned on via one of the modalities mentioned above as mechanisms of interaction with the device. Then, after the surgeon implants the IOL, the measurement of the wavefront continues. The surgeon adjusts the IOL position in the eye until the measurement confirms optimal placement of the IOL. Once the surgery is complete, the data is saved (if recording of data was turned on) and the system is switched off.

As an application embodiment, the presently disclosed apparatus can be used in cataract surgery to optimize the implantation of a conventional intra ocular lens (IOL). Initially, when the crystal lens is removed from the eye, the presently disclosed apparatus can be used to confirm the aphakic condition throughout the entire corneal visual field through dynamically changing the annular ring size. With an IOL implanted, as the defocus offset is tuned, the digital gain of the 2D data point position relative to origin of the x-y coordinate system on the display can also be increased or decreased to enable the end user to "zoom in" and "zoom out" and hence "magnify" or "de-magnify" the 2D data point pattern. In the case of a pure spherical refractive error correction, by changing the defocus offset, the diameter of a circle-like 2D data point pattern can be controlled by the end user to ease the centering of the 2D data point pattern relative to a reference point (such as the origin) of the x-y coordinate system and hence to achieve a better positioning accuracy of the IOL in the eye. The circle size can be changed per the need of the refractive surgeon by changing the defocus offset as well as controlling the digital "zooming", and as a result, the positioning precision of the implanted IOL can be substantially improved by moving the IOL until the circular 2D data point pattern is centered with respect to the reference point (such as the origin) of the coordinate according to some predetermined criteria. The "closing in" or "collapsing" of the scattered data points, especially with the help of the "zooming in" function through a digital gain control will help the fine positioning of the IOL, and at the same time the drive signal that corresponds to the best "zoomed in" closing of the data points will precisely indicate if the correction of the spherical refractive error is precisely achieved. This process of finding the best centering position can be automated also using a built-in algorithm.

As still another application embodiment, the presently disclosed apparatus can be used to indicate if an implanted multi-focal IOL has the desired focusing range in addition to optimizing its positioning. As is known to those skilled in the art, a multi-focal lens usually has a number of concentric annular zones with each annular ring having a different focusing power. Generally, as the zone gets further away from the center and closer to the outer peripheral region, the width of the annular ring gets narrower. In US20080278683, it has been mentioned that by using an adaptive sequential wavefront sensor to do the wavefront measurement, one can adjust the sampled annular ring diameter and the annular ring width by controlling the scan mirror tilt angle and the sub-wavefront sampling aperture size so that the sampled subwavefronts can be made to match with the different annular zones of the implanted multi-focal IOL. The presently disclosed apparatus can therefore be used to measure the wavefront from each annular zone individually and a live display/feedback of the measurement result combined with a proper defocus offset and also if needed, with accommodation change, can tell the refractive surgeon if the desired spherical refractive error correction for a particular zone is achieved. When the focusing power of each individual zone is obtained, the overall focusing range of the implanted multi-focal lens can also be determined. The surgeon will therefore be able to tell if the surgery is successful in terms of increasing the focusing range of the patient to the specified degree or extent.

Figure 14:
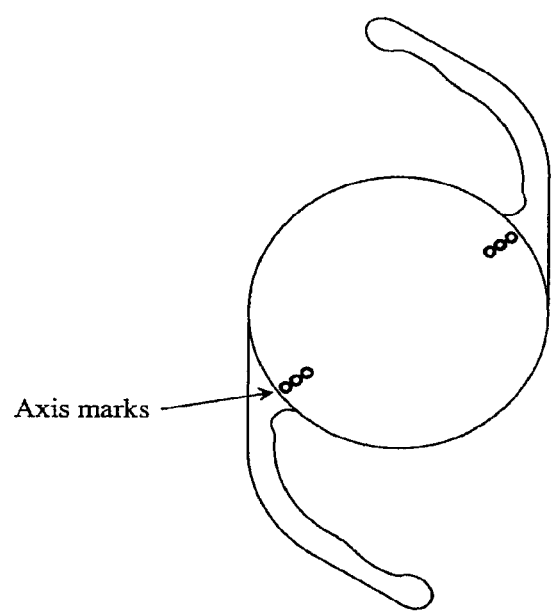
FIG. 14 shows a schematic diagram of a toric lens that has axis marks.

As a key application embodiment, the presently disclosed apparatus can be used to optimize the implantation and orientation of a toric IOL. In implanting a toric IOL during a cataract refractive surgery, in addition to the centering and tilt optimization of the toric IOL, a critical step is in rotating of the toric IOL to a desired orientation axis so that a complete correction of astigmatism can be achieved. The digital "zoom in" feature can become most useful for the toric IOL implantation procedure. FIG. 14 shows a schematic diagram of a toric IOL that has axis marks. As one aspect of an embodiment, the defocus can be offset to turn the 2D data point pattern on a display into a straight line and as a result, any remaining astigmatism can be shown with more detail. At this stage, the implanted toric lens can be rotated so that the displayed 2D data point straight line is turned into a circle. The defocus can then be further tuned to further try to turn the 2D data point display into a straight line and the "zoom in" feature can now be utilized while the toric IOL is being further rotated to change the straight line to a circle. This process can be repeated until a certain predetermined criterion has been reached. By rotating the implanted toric IOL to convert the straight line or ellipse to a circle and also fine tune the defocus with digital "zooming in" to make sure that the circle can be "closed" at the reference point or origin of the x-y coordinate, the desired position and angular orientation of the implanted toric IOL can be more precisely surgically determined.

As still another application embodiment, the presently disclosed apparatus can be used to check if an implanted accommodating or accommodative intra ocular lens (AIOL) can provide the desired accommodation range. As is well known to those skilled in the art, an AIOL is a lens that can change its focusing power in the eye under the action of the ciliary muscle. During AIOL implantation, in addition to centering the AIOL, if the ciliary muscle can still function, the patient can be made to accommodate at different distances with the help of the variable internal fixation. Otherwise, other ciliary muscle stimulation mechanism can be used to enable the accommodation change. By scanning the defocus offset and also doing a real time wavefront measurement, a more accurate measurement of the refractive errors along the full accommodation range of the implanted AIOL can be obtained. This will indicate whether the desired ciliary muscle enabled accommodation range has been reached with the implantation of the AIOL. The same measurement can also be done after the surgical operation when the patient has restored his/her accommodating capability.

As another application embodiment, the presently disclosed apparatus can also be used to provide a therapy for presbyopia, and to maximize surgical results after AIOL implantation. It is known to those skilled in the art that the inherent physiologic mechanism of accommodation is the same both for natural accommodation and for AIOLs. The capability of the presently disclosed apparatus to detect changes in the accommodation of the patient while obtaining real time wavefront measurement results may be used via a biofeedback mechanism to the patient, to enhance residual capabilities and thereby to delay the onset of presbyopia and to treat presbyopia once it begins.

After a surgery, a patient with an implanted AIOL can also utilize real-time biofeedback information to enhance the functioning of the lens through psychophysical feedback. In other words, the apparatus can record the complete optical condition of the eye in real-time, collect and analyzes the data and feedback the results to the patient to maximize performance of AIOL. The feedback can be derived based on real-time wavefront information and real-time measurement of the accommodation range or amplitude. The feedback can also be in the form of raw data, derived maps of information related to amplitude of accommodation, and/or other sensory inputs controlled by maximizing accommodation (including visual, auditory, olfactory, tactile, and/or gustatory feedbacks).

As still another application embodiment, the presently disclosed apparatus can be used to shape and position corneal onlay or inlay. It is well known to those skilled in the art that a biocompatible material can be implanted as an inlay or onlay into or onto the cornea and can be ablated with either excimer or femtosecond laser energy, or by other precise ablation technology. Such an ablation can enable an accurate and reversible refractive procedure that can eliminate the complications of ectasia and possibly post-op dry eye. The presently disclosed apparatus can thus be used to optimize the ablation or the manufacturing of the inlay or onlay to achieve optimal visual performance. The modification to the "blanks" can be performed either before or after implantation into or on the eye. There are many possible materials that can be used, including artificial collagen, with or without cross linking, potentially being cross linked into the surgical bed of the patient's cornea, or various hydrogels and advanced polymers. The specifications of the material can be determined to optimize function with real-time wavefront measurement as well as biocompatibility, reversibility, subsequent refinement, and optical performance. For example, the specification of the material can be set such that it can be modified and/or manufactured with a relatively inexpensive technology (e.g. laser or electromagnetic radiation of any optimal wavelength that can be delivered safely ex-vivo since there is no interaction with the patient's eye, and is much less expensive than excimer or femtosecond lasers).

The real-time wavefront data provided by the presently disclosed apparatus can be used to measure the eye aberrations, perform closed-loop real-time ablation or creation of the inlay or onlay ex-vivo (both anterior and posterior surfaces), and then implant the product under real-time intra-operative wavefront validation for accurate positioning. In this manner, the patient's eye is never exposed to laser irradiation, and the procedure is completely reversible. The inlay or onlay can be removed completely, with a new implant performed. Alternatively and in addition, refinement surgery can be performed on the inlay or onlay material at any time in the future. As another option, the inlay or onlay can be put into place first, and then real time wavefront data can be used to perform closed-loop real-time ablation of the inlay or onlay in-vivo. Clinically, all these approaches result in a reversible procedure that is enabled through real-time and accurate wavefront measurement provided by the presently disclosed apparatus. The intra-operative portion of the procedure is made possible through accurate positioning of the inlay or onlay using the presently disclosed apparatus. The additional clinical advantage with ex-vivo procedure is that energy is not delivered to the eye, and this will reduce the incidence of post-op dry eye or other post-op complications.

Figure 15:
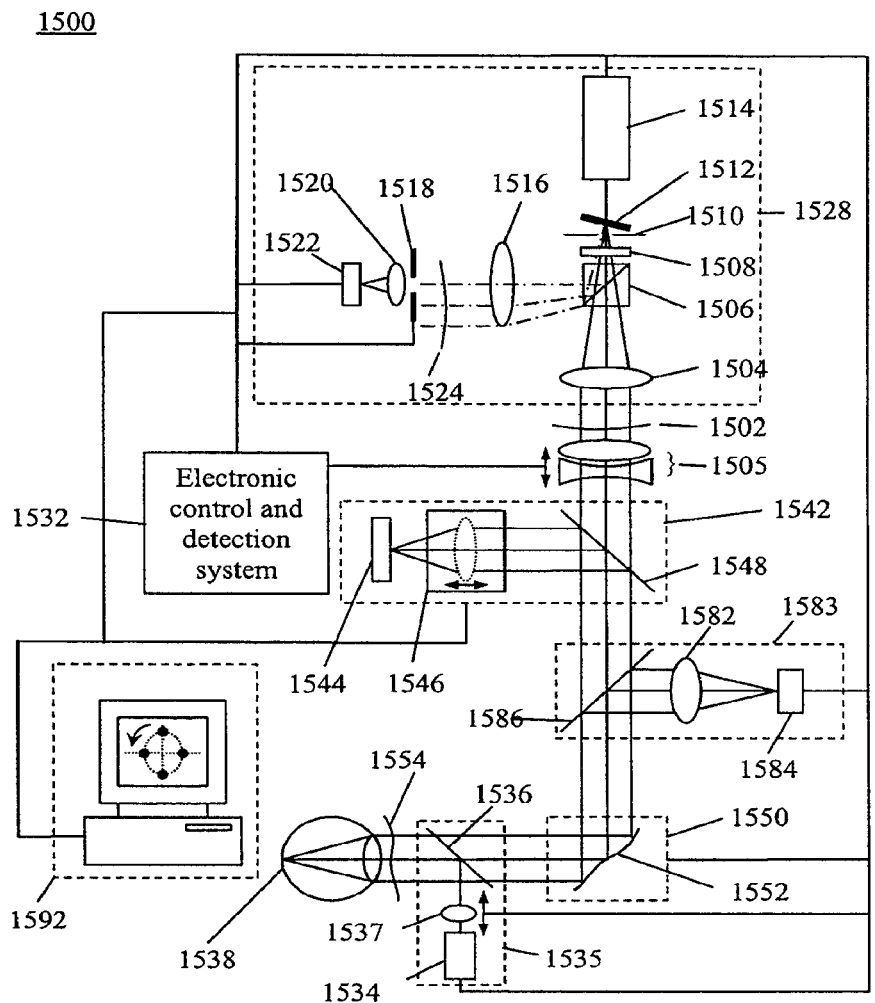
FIG. 15 shows a schematic diagram of another embodiment in which a dynamic wavefront manipulation device is used to offset some selected aberration components of the wavefront.

FIG. 15 shows a schematic diagram of another embodiment in which a dynamic wavefront manipulation device is used to offset some selected aberration components of the wavefront from an eye. The light source module 1535, the infrared imaging module 1583, the internal fixation/visual acuity projection module 1542, the real time wavefront sensor module 1528, the electronic control and detection module 1532, and the display module 1592, serve a similar function as 535, 583, 542, 528, 532, and 592 shown in FIG. 5. The light source module 1535, comprising the light source 1534, the collimating lens 1537 and the beam directing element 1536, is used to direct a narrow beam of light onto the retina of a patient eye 1538. It should be noted that some of these modules are not absolutely required for the functioning of the apparatus as have been discussed before. In FIG. 15, besides the active defocus offset element 1505, a wavefront manipulation module 1550 is added, which in FIG. 15 is shown as a deformable mirror 1552. The reason for the inclusion of the defocus offset element 1505 in addition to the deformable mirror 1552 is that generally speaking a deformable mirror has relative small stroke which means that its defocus offsetting range is limited. Therefore, a combination of a deformable mirror with a defocus offsetting element will enable one to achieve wavefront manipulation over a large practical range as the defocus or spherical refractive error variation is the largest of all wavefront aberrations among different eye. However, it should be noted that if the wavefront manipulation module 1550 does have a high enough dynamic range, then there is no need for the defocus offset element 1505. So the defocus offset element 1505 is not an absolutely required element for the function of embodiment shown in FIG. 15.

Note that the embodiment shown in FIG. 15 is an extension of what is shown in FIG. 5. The concept is to offset some wavefront aberration components based on a real time wavefront measurement feedback in order to allow the remaining aberration components to show up more clearly. The difference between the embodiment of FIG. 15 and that disclosed in US20080278683 is that a wavefront manipulation module 1550 is arranged in the light path to provide offset. Previous embodiments only mentioned the compensation or nulling function of such an element. In the current embodiment, in addition to the compensation or nulling function, the wavefront manipulation module 1550 also provides active off-setting or partial compensation of only certain aberration components of a wavefront from the patient's eye. The active offset is at the disposal of the refractive surgeon or controlled by a built-in algorithm according to the real time display and/or feedback of the wavefront measurement. One aspect of the present embodiment is to scan the offset of certain aberration components within the wavefront measurement range with or without the accommodation change of the eye over the accommodation range so that a better and more precision measurement of the eye aberrations can be obtained.

It should be noted that although a deformable mirror is shown as the wavefront manipulation element in FIG. 15, other wavefront manipulation element can be used, including transmissive liquid crystal based wavefront manipulation device. One unique advantage of combining a transparent wavefront manipulator or corrector with a real time wavefront sensor is that one can achieve a really compact adaptive optics system.

The position of the wavefront manipulation element can be anywhere along the optical path as long as it serves the function of offsetting some selected wavefront aberration components. In fact, for a compact design the wavefront manipulation element can be designed together with other optical element(s) inside the wavefront sensor 1528. Such a real time adaptive optics sequential wavefront sensor can be made with a small form factor and thus integrated into a large number of optical imaging or measurement systems, such as a refractive surgical microscope. It should also be noted that although a sequential wavefront sensor 1528 has been illustrated in FIG. 15, other types of wavefront sensors can also be used as long as it can provide wavefront measurement, including Hartmann-Shack, Talbot-Moire, Tscherning, Ray-tracing, phase diversity and interferometric wavefront sensors.

An independent form of wavefront recognition and control is an intrinsic component of the presently disclosed device in that a separate optical path comprised of a local wavefront manipulator interacts with the return beam as a separate action in reducing and re-composing of the transported beam aberrations to produce defined measurements of the local slope changes carried within the return beam. The active manipulator introduces a local beam deflection or deformation that "matches" the opposite sign of the input beam thereby canceling out the original beam deflection as the beam is sensed and measured. The active beam manipulator has then captured the nature of the beam aberrations allowing an active sensing and isolation of each defined variable aberration. This then provides the capabilities of introducing or nulling certain of the aberrations with respect to all or selected existing aberrations. In this active on-going process the deterministic dynamic wavefront sensing system can then provide a basis for interrogating the relative impact of the existing aberrations on the active performance of the system being evaluated. The active local wavefront manipulator has the capability of an independent operation for both global and local facets of the aberration. The manipulator can be used in tandem with the linear spherical compensation optics to fully enhance and provide ranging measurement capabilities while actively evaluating the detailed composition of the wavefront irregularities.

The presently disclosed apparatus shown in FIG. 15 can provide real time wavefront measurement results and therefore be used to optimize intra-operatively those refractive surgical procedures that can correct higher order aberrations. For example, in the future, an IOL can be custom designed to correct higher order aberrations such as coma and in such a case, when such an IOL needs to be implanted into an eye, there will be a need to position it properly during the implantation. An apparatus as shown in FIG. 15 can be used to compensate for example the astigmatism while offsetting the defocus. As a result, higher order aberrations such as coma can be more clearly revealed in the 2D data point pattern with a certain defocus offset. The refractive surgeon can then fine tune the position of the higher order aberration correction IOL to ensure that the correction for higher order aberration is optimized. There may be cases in which the high order aberrations need to be corrected through laser ablation of the corneal tissue while the lower order aberration is to be corrected by implanting a toric IOL. This approach can benefit a cataract patient with both low order and high order eye aberrations. By correcting the lower order aberrations with a toric IOL, which typically is performed during cataract surgery, the corneal tissue material that is to be ablated to only correct higher order aberrations will be much less than that needed if all the aberrations are corrected by ablating the cornea.

All refractive surgical procedures that can correct higher order aberrations including LASIK, SBK, LTK, IntraLasik, FlEXi Lasik, PRK, LASEK, RK, LRI, CRI, and AK, can benefit from the presently disclosed apparatus. For these procedures, the wavefront can be sampled according to any sampling pattern so that information on some particular wavefront aberration components can be obtained. The whole wavefront can be covered and higher order aberration (HOA) content, such as coma, which is a very prevalent HOA that surgeons are becoming familiar with and have ways to deal with, can be highlighted and displayed in a format easily understandable by clinical practitioners. In fact, measurement of asymmetric aberrations under good centration conditions, or any collection of data points that did not track with a circle or ellipse or a line with inflections, would mean that there are other HOA caused effects. The presence of these asymmetric conditions should be the norm not the exception since HOA will always be present to a certain extent. Understanding and separating these terms from sphero-cylindrical condition will aid in assessing the practical surgical limits. The removal of these terms will allow a better understanding on how a surgery should be performed properly. This is of paramount importance and essentially will set the presently disclosed apparatus apart from all other current approaches.

As one aspect of an embodiment, the presently disclosed apparatus can be combined with any refractive surgical laser systems to provide real time wavefront measurement feedback and guide a refractive surgeon in optimizing the refractive procedure. For example, when a certain higher order aberration is orientation specific, offsetting some aberrations will highlight the orientation dependence of the high order aberration and with a real time wavefront measurement feedback, any otherwise undetected cyclotorsional movements of the eye, or rotational misalignment between the eye and laser can then be detected and the orientation corrected and confirmed (based on pre-op assessments). As another example, it is known that there can be post-operative decrease in contrast sensitivity resulting from induced higher order aberrations during corneal refractive procedures (such as LASIK). In order to minimize this unfavorable and negative outcome, the presently disclosed apparatus can be used to provide a real time wavefront measurement with partial compensation of lower order aberrations, thus enabling a refractive surgeon to clearly see if there are higher order aberrations that result during the laser ablation process and to minimize these higher order aberrations.

Figure 16:
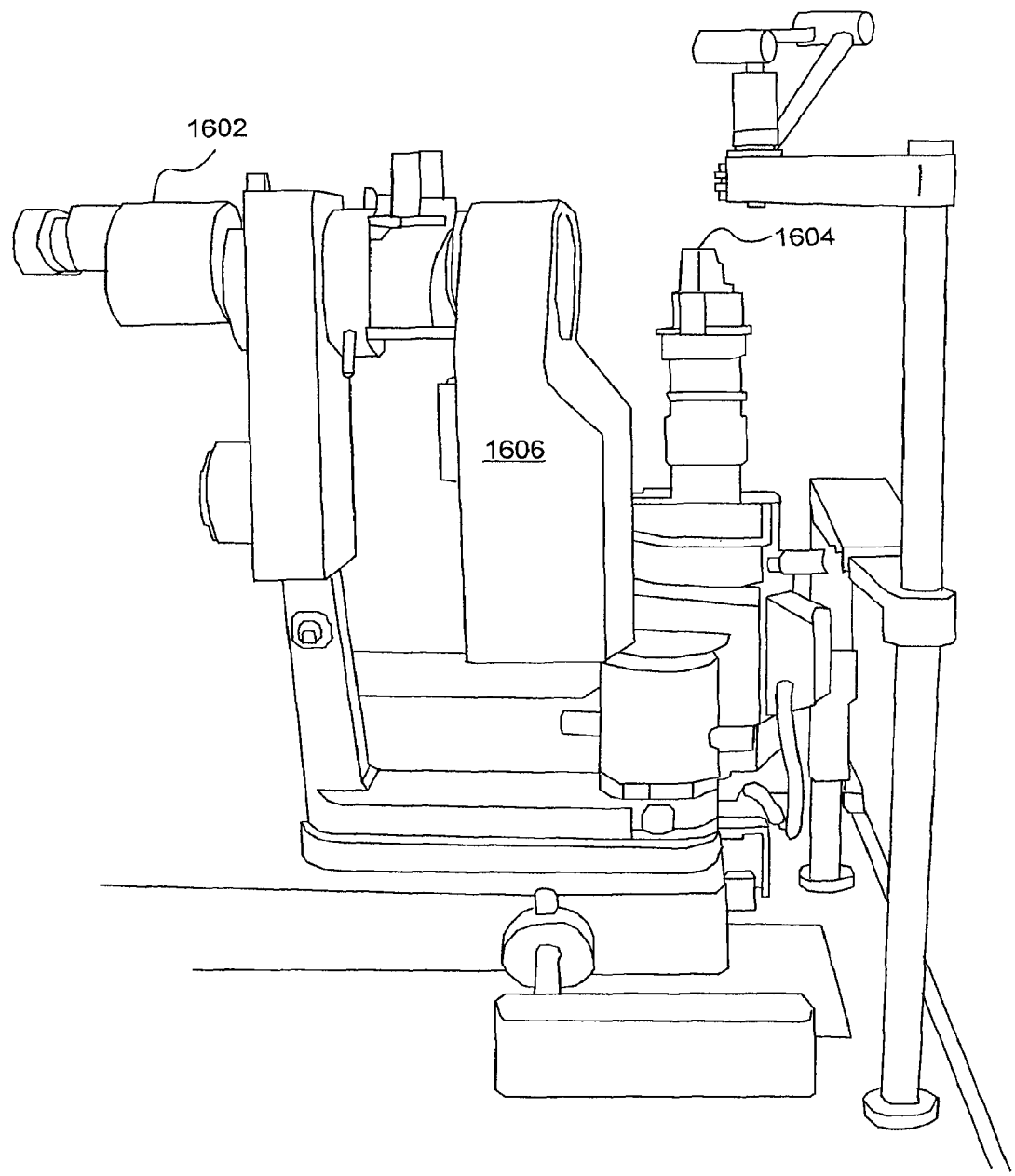
FIG. 16 shows an example embodiment of a wavefront sensor combined with a slit lamp examination apparatus

The presently disclosed apparatus can be incorporated into or combined with other ophthalmic devices as well to enhance their functionality. In addition incorporating such an apparatus in a surgical microscope to optimize a cataract refractive surgery, as another aspect of an embodiment, the same apparatus can also be combined with a standard slit lamp to provide both real time wavefront measurement and a slit lamp examination of a patient's eye. As depicted in FIG. 16, an example slit lamp examination apparatus includes a microscope 1602 and a slit lamp 1604 that can shine a focused slit of light on the patient's eye. A modular wavefront sensor 1606 is attached to the front of the microscope 1602 and configured to facilitate viewing the patient's eye and taking wavefront measurements.

For example, imagine that in the operating room at the end of a cataract case, the surgical microscope also captures a final wavefront measurement of the eye after IOL implantation. If there is residual astigmatism, the surgeon can perform either a limbal relaxing incision (LRI) or corneal relaxing incision (CRI) with the real time wavefront feedback to titrate the incision until the desired neutralization of astigmatism is achieved. Then, as the patient returns for follow up visits, a slit lamp that is combined with a real time wavefront sensor, as disclosed here and depicted in FIG. 16, will re-measure the same eye. The system will then be able to register the data from clinic measurement with the post-op measurement from the operating room at the end of the case, and look for regression over time. Based on the regression, the surgeon may recommend "enhancement" treatment, either back in the operating room, or in the clinic at the slit lamp. The clinic enhancement can be done under the same real time wavefront sensor's guidance as was available in the operating room. The titration of the enhancement procedure in the clinic can be under continuous real-time feedback, providing better outcomes, and developing a physician specific database of wavefront guided limbal relaxing incision (LRI) or corneal relaxing incisions (CRI) and intrastromal lenticule laser (Flexi) for further cylinder correction.

The above described embodiments can be used in a variety of applications. For example, it can be used in a lensometer to measure and fine tune the refractive power of a lens including a spectacle lens, a contact lens, and/or an IOL. Although various embodiments that incorporate the teachings of the present invention have been shown and described in detail herein, those skilled in the art can readily devise many other varied embodiments that still incorporate these teachings.

What is claimed is:

1. An apparatus for providing feedback during a vision correction procedure, with the vision correction procedure including implantation of an intra-ocular lens (IOL) by a practitioner, the apparatus comprising:
   a dynamic wavefront sensor configured to provide wavefront information characterizing a subject eye during a vision correction procedure, and configured to receive a portion of a wavefront and output position values from a subject eye, indicating the position of focused subwavefronts, with the portion of the wavefront comprising a plurality of subwavefronts; and
   a controller coupled to the dynamic wavefront sensor and a feedback providing device, configured to analyze wavefront information provided during rotation of an IOL, wherein the wavefront information includes centration conditions, to determine when the IOL is optimally aligned and configured to provide feedback to the practitioner when the IOL is optimally aligned.

2. The apparatus of claim 1, wherein the controller is coupled to the dynamic wavefront sensor, and configured to measure the portion of the wavefront and the output position values received by the dynamic wavefront sensor, and further configured to continue wavefront measurement of the subject eye with an implanted intraocular lens, and to facilitate adjusting the implanted intraocular lens position in the subject eye until a feedback confirms optimal placement of the implanted intraocular lens within the subject eye.

3. The apparatus of claim 1, with the controller further configured to provide audio feedback.

4. The apparatus of claim 3, with the controller further coupled to an audio signal device, with the controller configured to analyze wavefront information to determine ophthalmic characteristic of the subject eye and further configured to generate an audio feedback signal having specified pitch, tone or volume to indicate deviations of measured ophthalmic characteristics from target ophthalmic characteristics.

5. The apparatus of claim 4 wherein the controller is further configured to measure the cylinder error of the subject eye and the controller varies the pitch, tone and/or volume to indicate the deviation of the cylinder value from a target value.

6. The apparatus of claim 1 further comprising:
   a display; and
   with the controller further configured to provide visual feedback on the display indicative of an alignment of the implanted intraocular lens, and when the IOL is optimally aligned.

7. The apparatus of claim 6, wherein the visual feedback is highlighted with a font size, boldness, style, color, or combination thereof indicative of a level of correction.

8. The apparatus of claim 6, wherein the visual feedback comprises an ellipse configured to show spherical and/or cylindrical refractive error(s) of the portion of the subject eye.

9. The apparatus of claim 6, wherein the visual feedback comprises a circle configured to show spherical and/or cylindrical refractive error(s) of the subject eye.

10. The apparatus of claim 6, wherein the visual feedback comprises a straight line configured to show spherical and/or cylindrical refractive error(s) of the subject eye.

11. The apparatus of claim 6, wherein the visual feedback comprises alternating between a straight line and a circle configured to show spherical and/or cylindrical refractive error(s) of the subject eye.

12. The apparatus of claim 1, wherein the controller is further configured to calculate the centration conditions based on the wavefront and output centration position values received by the dynamic wavefront sensor.

13. An apparatus comprising:
    a surgical microscope configured to form an image of a subject eye at an object conjugate plane interior to the surgical microscope;
    a real time wavefront sensor configured to provide wavefront information characterizing the subject eye; and
    a micro-display disposed substantially at the object conjugate plane and configured to display the wavefront measurement information characterizing the subject eye such that the wavefront information is overlaid onto the image of the subject eye formed by the surgical microscope.

14. The apparatus of claim 13, wherein the micro-display is a semi-transparent micro-display.

15. The apparatus of claim 13, wherein the micro-display is positioned within an eyepiece of the surgical microscope.

16. The apparatus of claim 13, wherein the micro-display is a LCD monitor mounted directly onto the surgical microscope.

17. The apparatus of claim 13, wherein the real time wavefront sensor is further configured to receive a portion of a wavefront and output position values from the patient eye indicating the position of focused subwavefronts, with the portion of the wavefront comprising a plurality of subwavefronts.

18. An apparatus comprising:
    a surgical microscope having an eyepiece configured to focus an image of a patient eye on the retina of an eye of a user;
    a real time wavefront sensor configured to provide wavefront information characterizing the patient eye;
    a micro-display configured to display wavefront measurement information characterizing the subject eye; and
    a beam directing element, disposed in the imaging path of the surgical microscope, configured to project an image of the micro-display onto the retina of an eye of a user such that the wavefront information is overlaid onto the image of the patient eye formed by the surgical microscope and presented to the eye of the user.

19. The apparatus of claim 18, wherein the micro-display is a semi-transparent micro-display.

20. The apparatus of claim 18, wherein the micro-display is positioned within the eyepiece of the surgical microscope.

21. The apparatus of claim 18, wherein the micro-display is positioned external to the eyepiece of the surgical microscope.

22. The apparatus of claim 18, wherein the micro-display is a LCD monitor mounted directly onto the surgical microscope.

23. The apparatus of claim 18, wherein the real time wavefront sensor is further configured to receive a portion of a wavefront and output position values from the patient eye indicating the position of focused subwavefronts, with the portion of the wavefront comprising a plurality of subwavefronts.

* * * * *